US008731644B2

(12) United States Patent
Mehrotra et al.

(10) Patent No.: US 8,731,644 B2
(45) Date of Patent: May 20, 2014

(54) ECG DEVICE WITH IMPULSE AND CHANNEL SWITCHING ADC NOISE FILTER AND ERROR CORRECTOR FOR DERIVED LEADS

(75) Inventors: Ravi Mehrotra, New Delhi (IN); Ansari Imran Mohd, New Delhi (IN); Ashish Ranjan, New Delhi (IN); Deepti Chadha, New Delhi (IN); Anjali Sharma, New Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/255,833

(22) PCT Filed: Mar. 9, 2010

(86) PCT No.: PCT/IN2010/000134
§ 371 (c)(1),
(2), (4) Date: Sep. 9, 2011

(87) PCT Pub. No.: WO2010/103542
PCT Pub. Date: Sep. 16, 2010

(65) Prior Publication Data
US 2011/0319777 A1 Dec. 29, 2011

(30) Foreign Application Priority Data
Mar. 9, 2009 (IN) .............................. 445/DEL/2009

(51) Int. Cl.
*A61B 5/0428* (2006.01)
(52) U.S. Cl.
USPC ......................................................... 600/509
(58) Field of Classification Search
USPC ................................................ 600/509, 508
See application file for complete search history.

(56) References Cited

U.S. PATENT DOCUMENTS

| 4,958,640 | A | 9/1990 | Logan |
| 5,054,496 | A | 10/1991 | Wen et al. |
| 5,307,817 | A | 5/1994 | Guggenbuhl et al. |
| 5,411,031 | A | 5/1995 | Yomtov |

(Continued)

FOREIGN PATENT DOCUMENTS

JP  200333912  11/2003

OTHER PUBLICATIONS

Wikipedia.org, Nov. 28, 2007, XP002593165, URL:http://web.archive.org/web/20071128114922/http://en.wikipedia.org/wiki/Firmware, 2 pages.

(Continued)

*Primary Examiner* — George Evanisko
(74) *Attorney, Agent, or Firm* — Hiscock & Barclay LLP

(57) ABSTRACT

The present invention provides a device and method for filtering impulsive noise and channel switching noise at ADC in an ECG device with multiplexed ESCs. The filtering is based on an implementation of Burst Sampling technique also a method for correcting errors in derived leads caused by time delays due to sequential sampling of different ECG signals is also provided. Real time digital FIR filters are used for removing other types of noise in ECG signals. The ECG device is compact and light weight and includes features of self calibration, clip detection and drawing of power from USB port of a PC, batteries or an external power source. The ECG monitoring device of the present invention measures real time ECG signals with automated data recording, data storage and retrieval, data transmission/transfer to an external system, along with parameter extraction for ECG analysis in an efficient manner for quick and reliable ECG measurement, in an extremely cost effective manner.

16 Claims, 15 Drawing Sheets

(56) References Cited

U.S. PATENT DOCUMENTS

| | | |
|---|---|---|
| 5,503,159 A | 4/1996 | Burton |
| 2002/0091335 A1 | 7/2002 | John et al. |
| 2003/0055343 A1 | 3/2003 | Korhonen |
| 2005/0222511 A1 | 10/2005 | Hadley et al. |
| 2005/0281439 A1 | 12/2005 | Lange |
| 2006/0224071 A1 | 10/2006 | Stewart |

OTHER PUBLICATIONS

PCT, International Search Report, International Application No. PCT/IN2010/000134, Mailing date: Feb. 14, 2011, (17 pages).

ECG DEVICE WITH IMPULSE AND CHANNEL SWITCHING ADC NOISE FILTER AND ERROR CORRECTOR FOR DERIVED LEADS

CROSS REFERENCE TO RELATED APPLICATIONS

This application is a National Stage filing under 35 U.S.C. §371 of PCT Application No. PCT/IN2010/000134, filed Mar. 9, 2010. This application also claims the benefit of Indian Patent Application No. 445/DEL/2009, filed Sep. 3, 2009. The entirety of both applications is incorporated hereby reference.

BACKGROUND OF THE INVENTION

The present invention relates to a ECG (Electrocardiograph) device with Impulse and Channel Switching ADC Noise filter and an Error corrector for Derived Leads. The present invention more particularly relates to implementation of a Burst Sampling technique for removing Impulsive and Channel Switching ADC Noise from the ECG signal and an interpolation algorithm for correction of errors in Derived ECG Leads caused by sequential sampling of directly measured ECG leads. This invention in particular relates to a medical device for measuring, filtering, monitoring and recording ECG signals. It also relates to extracting some of the vital parameters using analysis functions built into firmware/software.

The expressions used in foregoing paragraphs including the background are explained below with reference to FIG. 1.

Einthoven Leads: Leads I, II and III are called Einthoven leads and represent the electrical potential difference between a pair of electrodes. The electrodes that form these signals are located on the limbs—one each on the left arm (LA) and the right arm (RA) and one on the left leg (LL). The Einthoven leads form a vector triangle known as Einthoven's triangle. If any two Einthoven leads (two sides of Einthoven triangle) are known, the third one can be derived by vector addition using the closure property of Einthoven triangle.

Augmented Limb Leads: Leads aVR, aVL, and aVF are augmented limb leads. They are derived from the same three electrodes as Leads I, II, and III and involve a rotation of axes.

Chest Leads: V1, V2, V3, V4, V5, and V6 are chest leads. These represent electric potential differences between electrodes placed on various points across the chest and the Einthoven's Reference Potential (see below).

Derived Leads: Here, Lead III, aVR, aVL, and aVF are derived leads as they are being derived from Lead I and Lead II by using vector addition and axes rotation.

Einthoven's triangle: An imaginary equilateral triangle having the heart at its center and formed by lines that represent the three standard limb leads i.e leads I, II, and III. of the electrocardiogram.

Einthoven's Center Point: (ECP)—The center point of the Einthoven's triangle.

Einthoven's Reference Potential (ERP)—It is realized by taking the average of the three electric potentials at the LA, RA and LL. Einthoven's Reference Potential offers a reference point with respect to which chest leads are measured.

The ECG measuring device terminology used henceforth in this document is as follows:

Electronic Signal Channel (ESC)—The path in the electronic circuit, along which a selected ECG signal (for example, from the output of the multiplexer) flows through the various stages of analog electronic processing, is termed as an ESC. The number of different ECG voltage signals processed simultaneously is equal to the number of ESCs in the ECG device.

ECG Channel—An ECG channel refers to the display of the ECG signals, each corresponding to any one of the ECG leads. Thus, a multi-channel ECG displays a number of signals corresponding to different ECG leads simultaneously.

ECG Lead—Refers to the electric potential difference for a given configuration, e.g., the Einthoven's Leads, Augmented Limb Leads or the Chest Leads.

Leadwire—An electrocardiographic cable which physically connects one of the electrodes placed on the body surface to the ECG measuring electronic system.

Due to combination of many factors, for example, stress, dietary imbalances, irregular schedules, life style, etc., the percentage of the population suffering with heart diseases is increasing. The ratio of available doctors to number of patients, especially in the context of developing countries, is small. On the other hand, the infrastructure and medical instrumentation available is inadequate to cater to the needs of large populations in developing countries. Consequently, long queues of patients and helpless doctors trying to attend to a bit too many patients, within the limited time available to them, is a common sight. The capacity of the general masses to pay for medical tests and diagnosis is also very limited. Thus, there is a need for high throughput and low cost monitoring and diagnostic medical instruments. One such widely used medical instrument is an Electro Cardio Graph (ECG). An ECG measures the electrical activity of the heart captured over time through external skin electrodes. Moreover, whenever the symptoms of a heart disorder are felt by patients, they have to be rushed to the nearest hospital or medical practitioner, where the ECG of the patient needs to be recorded, resulting in a delay between the time of the occurrence of the event and the ECG recording. This delay must be avoided in crucial cases. A low cost and easy to use ECG device is thus desirable with a feature to transmit the recorded ECG to a hospital or doctor. For example, as many homes now have a PC, it would be natural to have a PC plug-in ECG module, whereby the recorded ECG could be easily transmitted over the internet. It would also be desirable to have a compact, light weight and portable but full featured ECG device which a general practitioner could carry in one's medical kit bag for use in emergency in field conditions. It has been further recognized that the effectiveness of ECG recording devices involves not only how well cardiac signals are measured and recorded, but also its ease of use and fast turnaround time. Many available compact palmtop ECG machines with a single ECG channel display only one Lead at a time and thus have low throughput. Several such low cost machines are further limited to measuring only one ECG-lead and thus provide limited information for medical diagnosis. Alternatively, to improve upon the throughput of the device, multi-ECG channel machines are used which in general either employ "ADC per ESC setup" or "Shared ADC setup". The "ADC per ESC setup" uses separate circuitry (amplifiers, filters, ADC etc) in hardware for each ESC for simultaneous measurement of the ECG voltage signals. This makes the device bulky and comparatively more expensive. The power consumption of the device also increases. The maintainability of the device decreases because of the increased number of hardware components used in the design. Moreover, in the multi ESC system, there are always small gain differences from one ESC to another which further dictates that the calibration for each of the many ESCs has to be maintained for adequate accuracy of measurement. Another shortcoming of the scheme is that any drift over time in calibration of individual ESC will cause errors for the derived leads. To reduce the number of hardware components and the power consumption and to further improve upon the relative ease of calibration, maintainability and portability of the device, the second approach namely "Shared ADC setup" can be used. In this scheme ECG signals are multiplexed to allow switching of the measurement electronics from one ESC to another automatically. The use of a Shared-ADC-setup ensures that any ADC error, if any, is the same for all the ESCs.

Generally two principle setups are used in this type of multichannel digital acquisition systems namely:
Model 1) Shared ADC with separate S/H (Sample and Hold circuit).
Model 2) Shared ADC setup with shared S/H.

In the case of ECG, some leads are often derived from other leads by appropriate linear combination of two of the measured leads. For derived leads, all the directly measured ECG leads must be sampled at exactly the same instant of time, because the linear combinations of two components of a vector measured at slightly different instants of time will introduce an error in the derived leads.

One way to address the need for sampling all the ECG leads at exactly the same instant of time is to use Sample and Hold (S/H) circuits separately for each ESC while still sharing the ADC (Model 1). An analog multiplexer is used to scan the S/H outputs, and a single ADC is used to convert the ECG voltage signals sequentially to produce a serial output signal. One of the shortcomings of this scheme includes the charge leakage currents in the S/H circuits, which cause additional gain differences from one ESC to another and hence dictates the use of proper calibration to be maintained for each of the various ESC. The second alternate approach to further reduce the number of hardware components uses one single S/H circuit (usually included in an ADC electronic chip) on shared basis for the entire ESC along with the shared ADC (Model 2). An analog multiplexer is used to select the (analog) input ESC. Sequentially, each ECG voltage signal from an ESC is stored in the S/H circuit and converted to digital format by the ADC.

This scheme offers the benefit of employing lesser number of hardware components. Minimizing the number of hardware components not only helps reducing the size and cost of the device, but also helps in improving the maintainability and reliability. The power consumption of the device also reduces which is a desirable feature for the portable devices. But there are two major concerns with this scheme (Model 2): (a) the ECG voltage signals from different ESCs are multiplexed, and hence not sampled at exactly the same instant of time. As some of the leads are derived from other leads, linear combinations of two components of a vector measured at slightly different instants of time introduce an error in the derived leads and
(b) when each ECG voltage signal is switched and sampled by ADC for digitization, there is always a possibility of a spike/glitch/impulse giving an erroneous reading. Spikes contain frequency components, some of which lie within range of frequencies of the ECG pass band and can not be removed by usual FIR filters. Impulsive noise is noise of short duration, particularly of high intensity, such as that produced by turning on/off of a high mains current device in the vicinity, power fluctuations etc. Moreover, charge injection by the switching of the analog multiplexer can also impose glitches on the S/H output. Channel switching, with the associated sudden voltage change in analog circuits, may also introduce effects like overshoot, undershoot and ringing etc., which may lead to further deterioration of the sampled signal. Both the schemes used in Model 1 and Model 2 of Shared ADC setup use multiplexing and switching of signals which may introduce "Channel Switching Noise".

In this invention, we address the first issue of errors in derived leads caused by sequential sampling of ECG leads in the "Shared ADC setup 2" by mathematical interpolation of the measured leads to the same instant of time. The second issue of spike/glitch/impulse, which have some frequency components in the ECG frequency pass band and can cause ringing effects in the measured signals once bandpass filters are applied to filter such noise, is addressed in this invention with the application of a burst sampling technique.

Reference may be made to Article: A suppression of an impulsive noise in ECG signal processing Pander, T.P. Engineering in Medicine and Biology Society, 2004. IEMBS '04. 26th Annual International Conference of the IEEE. Volume 1, 1-5 Sep. 2004 Page(s):596-599. Digital Object Identifier 10.1109/IEMBS.2004.1403228.

Biomedical signals are commonly recorded with accompanying noise. Many different kinds of noise exist in the biomedical environment. One of the components of noise is a waveform due to electrical activity of the muscles. This "natural" distortion is usually modeled with a white Gaussian noise. But such assumption is not always true, because real-life muscle noise has sometimes impulsive character. First objective of this paper is an application of the alpha-stable distribution as a model of the real-life muscle noise in the ECG signal. Second objective of this paper is an application of a family of M-filters to suppression an impulsive noise in biomedical signals (ECG signals). The reference filter is the median filter. This prior art relates to filtering muscle noise from the ECG signals by using M-filters. These filters are non-linear and computationally inconvenient. Also, the reduction obtained in muscle noise is at the cost of distortion in the ECG signal of interest. In our invention muscle noise is filtered with the linear digital FIR filters.

Reference may be made to Article: Spike detection in biomedical signals using midprediction filters. S. Dandapat and G. C. Ray Med. & Biological Engg & Computing, Volume 35, Number 4, July 1997, pp. 354-360.

Summary: Sudden changes in biomedical signals, such as the QRS complex in ECG, epileptic seizures in EEG, etc. are treated as spikes in a relatively slowly varying background signal. Detection of such "spikes" with minimal distortion is the objective of this work. Such spikes, because of their inherent high frequency content, appear as an error signal in a linear prediction scheme. A symmetric midprediction filtering scheme is proposed wherein the distortion of the detected spike as well as reliability of detection is improved. This prior art relates to treating the QRS-complex as a "spike" in the ECG signal and detecting it reliably with little distortion. This "spike" is the signal of interest to be detected. On the contrary, our invention relates to elimination of undesirable sudden noise spikes (higher in frequency than the QRS complex) in the ECG signal. Our invention typically filters out spikes of frequency equal to or above the burst sampling frequency.

Reference may be made to U.S. Pat. No. 5,999,845A "Muscle Artifact Noise Detector for ECG Signal" This invention provides detection and filtering system for detecting and filtering line noise, baseline wander, and wide band noise such as muscle artifact signals to maximize the filtering of noise signals. The Detector compares noise levels to threshold values and reports the resulting noise status to cancellation filters.—It further provides the operator with the ability to manually or automatically activate the filters and to indicate the status of the filters on a printout or display. This prior art requires blanking of the QRS complex for estimation of noise. Many filter implementations are of the IIR type which in principle can be unstable. Also, individual microprocessors are required for filtering of noise in each measured channel. Filters have to be activated automatically or manually by an operator.

Our invention does not require automatic or manual activation of filters by an operator. Instead, our method uses a series of filters like stable linear digital FIR filters along with Burst Sampling Technique for removing power line interference; spike/glitch, wide band noise and baseline wander noise in the ECG signal. No separate microcontrollers/microprocessors are required for each ECG signal measured.

Reference may be made to U.S. Pat. No. 5,908,393A "Reducing noise in a biological system": This prior art includes acquiring a biological signal, such as an ECG Signal, comparing it to a representative signal and generating a predicted signal. The predicted signal is subtracted from biological signal to produce a second signal. This second signal is passed through a filter to produce a filtered signal. The predicted signal and the filtered signals are then combined to produce noise reduced signal.

The filtering in our invention is independent of any representative or predictive signals. Reference may be made to U.S. Pat. No. 5,704,365A "Using related signals to reduce ECG Noise" The invention provides an improved technique for reducing noise in physiologic signals by using each signal as a vector projection of the underlying ECG generator onto the body surface and combines the signals in a manner that optimally reduces the noise while preserving the net vector direction of the ECG generator. In accordance with the principles of this prior art the process includes obtaining multiple input signals, measuring a relationship between noise content of the input signal, and combining the input signals in consideration of the measured relationship to produce an output signal having low noise content. This prior art relies upon measurement of secondary input signals representing noise. Noise filtering in our invention does not require measurement of any extra secondary signals representing noise. Reference may be made to U.S. Pat. No. 7,221,975B2 "Signal filtering using orthogonal polynomials and removal of edge effects": This prior art describes method of filtering an input signal containing wanted signal components and unwanted noise components, comprising modeling the input signal as a set of polynomials, identifying polynomials from the set to model the unwanted signal components, and removing the unwanted signal components from the input signal by removing the polynomials identified as modeling the unwanted signal components from the set of polynomials to thereby leave the input signal only the wanted signal components.

In the above prior art, the input signal and the unwanted noise have to be modeled by a set of polynomials, whereas our invention uses noise filters which do not require any modeling of the input ECG signals or noise.

Reference may be made to U.S. Pat. No. 5,269,313A "Filter and method for filtering baseline wander": The invention discloses a linear phase high pass filter using a linear phase low pass filter in parallel with an electronic delay for removing baseline wander from an ECG signal. A digital IIR filter is preferably used as the linear phase low pass filter.

The filtering methods used in above prior art depends on IIR filter which in principle can become unstable. It also employs an electronic delay and hence requires additional hardware for each measured ECG signal. Our invention employs stable linear FIR filters with no requirement of electronic delays.

Reference may be made to WO93/05574 "ECG Muscle Artifact Filter System": The invention discloses a methodology for filtering muscle artifact signals from an ECG signal. The ECG signal is passed through a LPF having variable cut off frequencies during the portion of the ECG signal exclusive of the QRS complex. At a time slightly prior to the onset of QRS complex, the cut off frequency is incrementally increases to higher cut off frequency to pass the QRS complex with a minimum reduction of amplitude of the QRS signal. At the end of the QRS signal, the cut off frequency of filter is incrementally returned to the low cut-off frequency. An adaptive filter with low cut off frequency is used to reduce Muscle Artifact (implemented in hardware).

The above prior art employs multi-module hardware (for electronic delay, R-wave detection system, smoothing filter and adaptive bandwidth control) for each of the ECG signal measurement channels to filter muscle artifacts. Our invention does not rely upon any additional hardware for filtering muscle noise. The digital firmware/software based FIR filters remove power line, muscle artifact and baseline wandering noise. In addition, the burst sampling based filter removes impulsive and channel switching ADC noise.

A study of the prior art reveals that the existing ECG monitoring devices do not address the removal of Channel Switching ADC Noise and glitches/spikes. The classes of multiplexed ECG signal measurement devices also do not address any method for correcting the digitized ECG signal points for time delay in switching between different channels. For example, some conventional monitors filter only EMG Noise, Power Line Interference, Baseline Wandering and background noise. Some of them use IIR filters which are not necessarily linear and, in principle, can be unstable. Some others employ complex multi-module hardware to achieve filtering of various types of noise. Some of the devices simply monitor and display ECG signals and thus provide no ECG data recording capability at all. Others record ECG data and provide only for the local playback of recorded data and thus provide no remote diagnostic capability. Still other devices use bulky and expensive hardware circuitry for calibrating the device, filtering the signal using analog low pass and high pass filters etc and for clip detection. Still others simply display and record the ECG data without calculating and displaying vital heart parameters at least in the monitoring grade device.

Thus, there is a need for compact, lightweight, portable, fast turn around time, and low cost monitoring devices for recording ECG signals. A provision of a configurable set of features/set-up options while maintaining user friendliness would be desirable. The specific features in a version of the device could be fine tuned according to end use. A facility to store the ECG records along with patient information, which can later on be used for further reference by the specialist, would also be needed. It has been recognized that it would be advantageous to provide a device which improves availability of basic medical care to general public by use of low cost modern electronics, automation and IT technology for monitoring equipment. It has also been recognized that it would be desirable to provide a device which could extract and display some of the important parameters related to ECG in the monitoring grade device itself using inbuilt firmware/accompanying software.

SUMMARY OF THE INVENTION

The main object of the present invention is to provide a compact ECG monitoring device which implements a procedure of utilizing a Burst Sampling technique for filtering Impulsive and Channel Switching ADC Noise and further implement an error corrector utilizing an interpolation technique for correction of errors in the derived leads caused by time delays due to sequential sampling of different ECG voltage signals in an ECG device with multiplexed ESCs which obviates the drawback of the hitherto known prior art as detailed above.

Yet another object of the present invention is to provide a generalized and hardware independent solution, which is implemented in firmware, for addressing both of these issues namely Impulsive and Channel Switching ADC noise and error in derived leads, which is related to the "Shared ADC setup Model 2".

Yet another object of the present invention is to provide an additional advantage of flexibility of up gradation as methods are generic, algorithmic and implemented in firmware. Up gradation of the device becomes a simple matter of upgrading the firmware rather than re-designing and re-building the circuitry/hardware.

Yet another object of the present invention is to provide the self calibration without incorporating on board electronic circuits for a tunable precision amplitude oscillator or the use of an external oscillator. An ECG device is usually calibrated with a 1 mV amplitude AC signal in the frequency range of the device (10 Hz).

Accordingly, the present invention provides an ECG device with Impulse and Channel Switching ADC Noise filter and Error Corrector for Sequential Sampling of ECG signals. The device is light weight, portable, convenient, high throughput and low cost to allow standard ECG measurements.

In one embodiment of the present invention an Electro Cardio Gram (ECG) device with impulse and channel switching analog to digital converter (ADC) noise filter and an error corrector for derived leads comprising the combination of ECG electrodes and leadwires (1) for measuring ECG signals and to determine the derived leads therefrom, an ECG module (2) coupled to the ECG electrodes and lead wires (1) for receiving the measured ECG signals therefrom and for digitizing the ECG signal, a user interface module (3) coupled to the ECG module (2) and power unit (4) coupled to the ECG module (2) for providing electrical power thereto, characterized in that the said ECG module (2) is provided with a firmware, wherein said firmware utilizes a burst sampling technique for filtering impulsive and channel switching ADC noise in digitized ECG signals, followed by error corrector utilizing an interpolation technique for correction of errors in the derived leads caused by time delays due to sequential sampling of the ECG signals received from Electronic signal Channel (ESCs) in the ECG module (referred to as the directly measured ECG signals) and finally providing high order FIR filter utilizing convolution technique to remove noise outside the ECG pass band.

In yet another embodiment of the present invention wherein ECG module (2) comprising:
a) an isolation buffer (2.0) to provide the isolation of the ECG signals picked up by the electrodes and leadwires (1);
b) a multiplexer (2.1) coupled to the isolation buffer (2.0) to receive buffered ECG signal therefrom, the multiplexer adapted to switch from ECG acquisition to calibration mode during device self-calibration cycle;
c) a signal conditioning and amplifier unit (2.2) coupled to the multiplexer (2.1), the signal conditioning and amplifier unit comprising pre-amplification instrumentation amplifier (2.2.1), band limit filter (2.2.2), and post amplification and level shifting (2.2.3), wherein the said band limit filter is a combination of first order high pass and low pass analog filters;
d) an averaging circuit (2.3) to calculate ERP (Einthoven's Reference Potential) in order to measure chest ECG signals with a reference thereto;
e) a calibration unit (2.4) coupled to the multiplexer (2.1), the calibration unit (2.4) comprising a voltage reference IC (2.4.1) and precision potential divider (2.4.2) to generate 1 mV DC signal that is supplied to the multiplexer for subsequent conversion, by chopping at the multiplexer, to a 1 mV square wave calibration signal with frequency within the pass band of ECG monitoring device;
f) an ADC (2.5) coupled to the signal conditioning and amplifier unit (2.2) and adapted to convert the amplified ECG signal voltages to produce digital data representative of patient's ECG waveform over a defined interval of time;
g) a control unit along with the firmware (2.6) coupled to the ADC (2.5), adapted to control and read data from the ADC (2.5), monitor and set the status indicators of the power & data indicator (2.7), control the multiplexer unit (2.1) via uni or bidirectional communication as applicable and adapted to filter the digitized directly measured ECG signals received from the ADC (2.5);
h) a power and data indicator (2.7) to visually indicate the error status of the power unit (3) and the run state of the ECG module (2);
i) a communication channel (2.8) which is any one or a combination of SPI, USB, USART, RS-232, Bluetooth, zigbee, ethernet and used to communicate with the user interface module (3);
j) a memory unit (2.9) coupled to the communication channel, to store and retrieve patient's digitized ECG waveform;

In yet another embodiment of the present invention wherein the measured ECG signals received from the human body via ECG electrodes and lead wires (1) comprises left arm, right arm, left leg and chest ECG signals; wherein these ECG signals are being input to an isolation buffer (2.0); wherein the left arm, right arm and left leg ECG signals are being input via an isolation buffer (2.0) to an averaging circuit (2.3), whose output is the ERP (Einthoven's Reference Potential) for measuring the chest leads; wherein said buffered ECG signals and the calibration signal from calibration Unit (2.4) are used as input to multiplexer (2.1); wherein output of said multiplexer being used as input to signal conditioning and amplifier unit (2.2) which provides amplified output in the required frequency range to an ADC (2.5), the output of said ADC being used as input to control unit (2.6) for removal of impulsive and channel switching ADC noise by using Burst sampling technique and correction for time delay due to sequential sampling of directly measured ECG signals using an interpolation method; wherein the ESC (electronic signal channel) wise calibration constants are computed with the multiplexing unit (2.1) in the calibration mode and wherein the digital and filtered output of said control unit being used as input to the User Interface Module (3) via communication channel (2.8); wherein the said digitized and filtered ECG signals are being stored and retrieved from memory unit (2.9).

In yet another embodiment of the present invention wherein, Burst Sampling technique is being implemented in the control unit (2.6) for removing impulsive and channel switching ADC noise from the digitized directly measured ECG signal, comprising the steps of:
a) scanning all the multiplexed n ESCs (Electronic Signal Channels) for one set of readings, by sending n ESC selection pulses to the ADC from the control unit, wherein n is equal to the number of multiplexed ESCs;
b) obtaining a burst of m digitized samples, for a given scanned ESC i, from the ADC where m denotes no. of sampling pulses and the said m digitized samples being numbered as $y_{i,1}, y_{i,2}, \ldots, y_{i,m}$, each after time interval $t_s$ (burst sampling time);

c) sorting all the m digitized samples for a given ESC i;

d) calculating weighted average of the median and mean of m digitized samples to give one filter digitized value for the scanned ESC i channel wherein the weight factors for the mean and median are w and (1−w) respectively, which together sum up to unity;

$$y^{-i} = w<y^i> + (1-w)y_{median}^{i} \quad (1)$$

e) optionally in place of calculating weighted average of median and mean of m digitized samples, carrying out a partial median computation followed by the mean operation by discarding maximum and minimum values of m digitized samples and calculating mean of remaining m−2 values, in case sorting for the median operation is time consuming in the context that the control unit (2.6) must complete scanning and processing of the signals received from n ESCs within the time available for one scanning cycle.

In yet another embodiment of the present invention wherein errors in calculation of derived ECG leads due to sequential sampling in time of directly measured ECG leads are corrected by using values of the directly measured ECG signals interpolated to the same instant of time; wherein the interpolated values are calculated utilizing an interpolation algorithm comprising the steps of:

a) obtaining the digitized and filtered (with burst sampling technique) value $y^{-i}$ for a given ESC i corresponding to a time ($it_{ch}$) relative to the time at which the first ESC is measured in the current scanning cycle;

b) interpolating all the filtered digitized values $y^{-i}$ for the n channels to a reference time, ($i_0 t_{ch}$) corresponding to ESC number $i_0=n/2$ to minimize interpolative corrections;

c) calculating interpolated value $y^{-i}_c(i_0 t_{ch})$, in terms of the current filtered value $y^{-i}(i_0 t_{ch})$ and the filtered value in the previous scanning cycle $y^{-i}(i_0 t_{ch}-i_s)$, by using the linear interpolation formula given below:

$$\overline{y}^i_c(i_0 t_{ch}) = \overline{y}^i(it_{ch}) + (i-i_0)[\overline{y}^i(it_{ch}) - \overline{y}^i(it_{ch} - \tau_s)]\frac{t_{ch}}{\tau_s} \quad (2)$$

In yet another embodiment of the present invention wherein user interface module (3) consisting of (a) a visual graphics display, such as an LCD/Mobile phone screen/PC monitor, to visually display the ECG signals, extracted parameters, and warning and error conditions if any (b) an input device such as keyboard, keypad, mouse, to control the ECG device, enter commands for various operations and enter patient data, etc. and (c) output devices such as a printer to provide a hardcopy of the ECG signals and extracted parameters, audio output for warnings and error conditions, wherein said user interface module (3) communicates with the memory unit and the control unit (2.6) via the communication channel (2.8) of the ECG module (2).

In yet another embodiment of the present invention wherein the power unit (4) comprises of a power source (4.1) and an isolation chip (4.3) in case the power source is directly/indirectly connected to AC mains, or a battery (4.2) and a voltage inverter, wherein said power source provides voltage output in the range of 3V to 5V to supply electrical power to the ECG module (2).

In still another embodiment of the present invention a method for measuring and monitoring the electrical activity of heart using the ECG monitoring device, the method comprising the steps of:

a) connecting ECG electrodes and leadwires (1) to patient;

b) illuminating the power and data indicator (2.7) after turning on the device;

c) initializing all the hardware components of ECG monitoring device including communication bus, timers etc. automatically by control unit (2.6);

d) configuring timer interrupt for ECG data sampling by control unit (2.6);

e) generating 1 mV dc output as a calibration signal by calibration unit (2.4), converting this to a 1 mV square wave at a selected frequency in the ECG pass band by chopping by the multiplexer unit (2.1), and feeding the converted calibration signal to the circuit along the same route of amplifiers and filters etc. as the ECG signal;

f) storing the digital count, for each ESC, corresponding to 1 mV calibration signal amplitude as calibration constants by the control unit (2.6);

g) passing the electrical signal measured by electrodes via isolation buffer (2.0) (which provides isolation of signals) and also via an averaging circuit (2.3) to provide ERP (Einthoven's Reference Potential) for measuring chest signal with a reference point upon initiation of operation of the ECG monitoring device by a user;

h) providing calibration signal, ERP and ECG signals from electrodes as input to multiplexer (2.1) in order to arrange routing of said signals to three ESCs (Electronic Signal Channel);

i) providing output of the multiplexer (2.1) to Signal Conditioning and Amplifier unit (2.2), which outputs the signal in the required frequency range typically from 0.22 Hz to 100 Hz and typical gain of 1000;

j) applying output of Signal Conditioning and Amplifier unit (2.2) to 12 bit precision ADC (2.5);

k) receiving of ESC selection signals and receiving of ADC conversion trigger by the ADC (2.5) from control unit (2.6) to digitize the output of Signal Conditioning and Amplifier unit (2.2);

l) applying filtering for removing impulsive and channel switching ADC noise by using 'Burst Sampling' technique from the output of ADC (2.5) by control unit (2.6);

m) checking for underflow and overflow of ADC (2.5) for clip detection by control unit (2.6);

n) applying linear interpolation by control unit (2.6) for correcting errors due to non simultaneous sequential sampling of directly measured ECG signals;

o) temporarily storing digitized and filtered data into the data buffer of control unit (2.6);

p) building data frame by adding header and footer into the stored digitized and filtered ECG data after data buffer is full;

q) communicating data frames to the user interface module (3) through communication channel (2.8) by control unit (2.6) and reinitializing the data buffer of control unit (2.6);

r) parsing data frames to detect and correct transmission errors if any;

s) applying further filtering which uses real time digital FIR filters using convolution onto parsed data frames to ensure that only ECG data in the frequency band 0.3 to 32 Hz is retrieved;

t) plotting filtered data from output of FIR filters on the output device such as LCD/mobile phone/PC screen;

u) recording and storing of filtered ECG data onto memory unit (2.9) such as MMC, hard disk, phone memory along with patient information for future reference by using platform independent graphical user interface;

v) extracting vital ECG parameters such as Heart Rate, RR Interval, PR Interval, QT Interval, QRS Width, and QRS Angle from recorded ECG data by using analysis software.

w) printing of ECG report.

In yet another embodiment of the present invention wherein, the noise in the directly measured ECG signal is removed at three stages in sequence, the stages being:

a) at the first stage, implementing a hardware based analog band limit filter (2.2.2) in the signal conditioning and amplifier unit (2.2) to filter out DC offsets and frequencies above Nyquist frequency to prevent aliasing effects, which attenuates noise at frequencies above the Nyquist frequency in the digitized ECG signals from ADC (2.5) folding back into the ECG pass band frequencies when the FIR filters are applied later at the third stage, wherein the required pass band frequency is in the range of 0.22 Hz to 100 Hz;

b) at the second stage, implementing burst sampling filter in the control unit (2.6) to filter out noise consisting of spikes/glitches/impulses, thus removing such noises completely or attenuating it so that the ringing or oscillations caused by application of FIR filters (at the third stage) to impulses are reduced;

c) finally at the third stage, implementing real time digital linear band pass filtering, FIR filters, using convolution techniques in the control unit or externally on a PC/Laptop to filter base line wander, EMG noise, power line noise and other noises outside the ECG pass band of frequencies in the range of 0.3 Hz to 32 Hz.

In yet another embodiment of the present invention the ECG pass band frequency range can be extended to 0.05 Hz to 150 Hz by suitably modifying the cut off frequencies of the various filters and using a notch filter at the power line frequency, for better accuracy in the measurement of S-T segment and high frequency content of the QRS complex.

In yet another embodiment of the present invention the order of the analog and FIR filters can also be varied and tuned depending upon the actual electronic circuit used and the nature of noise present therein.

In still another embodiment of the present invention wherein analysis software being employed offline to extract the vital parameters of ECG signals comprises the steps of:

a) selecting two ECG lead signals from recorded and stored ECG Leads I, II and III with largest rms value;

b) applying high order FIR low pass filter with cut off frequency at least 20 Hz on selected two ECG lead signals to get smoothened ECG lead signals;

c) applying numerical differentiation on obtained smoothened ECG lead signals to get derivative ECG signal;

d) converting obtained derivative ECG signal to MOBD (multiplication of backward differences) ECG signal;

e) applying adaptive threshold algorithm on obtained MOBD ECG signal to locate and identify QRS complexes;

f) computing weighted derivative of smoothened ECG lead signals;

g) locating and identifying P-wave and T-wave, using the computed weighted derivatives as is in step (f), corresponding to each identified QRS complex;

h) computing RR-interval, heart rate, PR interval, QT interval and QTc, ST segment, QRS angle and the standard deviation in each of the measured quantity by using original, that is, before application of additional filtering in step (b) values of ECG lead signals in the frequency range 0.32 to 32 Hz.

In still another embodiment of the present invention characterized in that the burst sampling technique being embedded in firmware is utilized in removing impulse and channel switching ADC noise from ECG signal.

In still another embodiment of the present invention characterized in that the linear interpolation technique being embedded in firmware is utilized for correcting error in derived ECG leads due to sequential digital sampling of the measured ECG leads.

In still another embodiment of the present invention, wherein it includes an anti-aliasing Band Limit Filter before post-amplification and digitization of the signals.

In yet another embodiment of the present invention wherein real time FIR Digital Filters used to remove various types of noises such as Base Line wanders, Power Line interference, EMG Noise etc. from the ECG Signals.

In yet another embodiment of the present invention wherein a method for obtaining electrocardiogram (ECG) waveforms from a patient includes coupling at least 5 electrode leadwires to the monitor module on one side and the patient on the other and further includes processing inputs from the electrode leadwires, framing the signal to detect and correct errors if any in the signal as well as to provide demarcation, transferring the data frames to the User Interface Module (PC/laptop, etc.) using some communication mode (USB/bluetooth/Zigbee/RS-232, ethernet, etc.) and storing/recording the processed ECG data in memory.

In yet another embodiment of the present invention wherein it includes a method for deriving augmented Leads (aVR, aVL, aVF) and Lead III from Lead I and Lead II measurements. The method further includes self calibrating the device and powering the device through the USB port of the Personal Computer/Laptop in case the PC/Laptop is used as a User Interface. Otherwise the power will be supplied by batteries or an external power source. It also includes on-line real time displaying of the ECG signals on the monitor of the PC/laptop/LCD Display/mobile or any user interface for that matter.

In yet another embodiment of the present invention wherein it includes recording the ECG data along with the personal details of the patient to the memory which can be retrieved later on for further reference and analysis. The minimum and maximum duration for the recording of ECG data is configurable.

In yet another embodiment of the present invention wherein the software built into the PC/laptop for displaying and recording the ECG data along with entering the personal information of the patient may be installed on any desktop or laptop computer that has, for example, USB connection capability. The software can run on a wide range of operating systems, for example, the Windows Me/2000/XP/Linux operating system.

DETAILED DESCRIPTION OF THE PRESENT INVENTION

Figure 1:
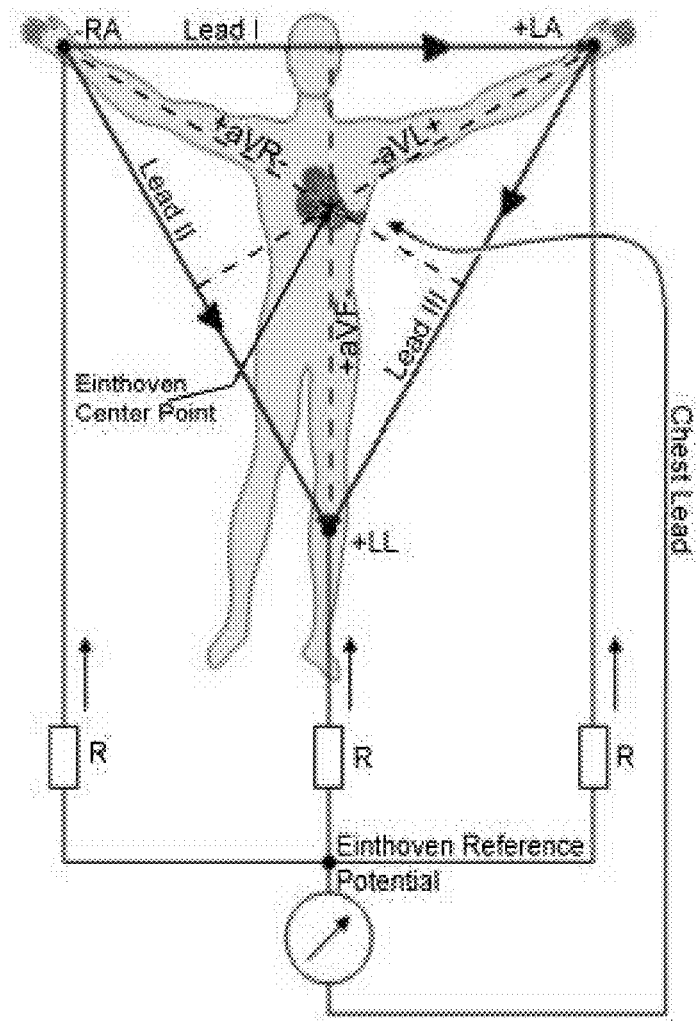
FIG. 1 is a diagram illustrating standard ECG terminology
Figure 2:
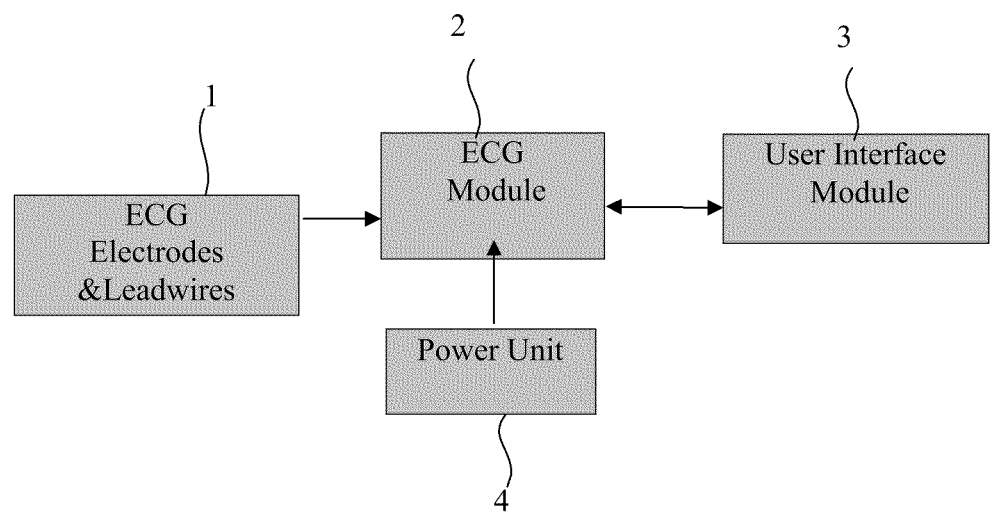
FIG. 2 is a block diagram illustrating an ECG Monitoring Device.
Figure 5:
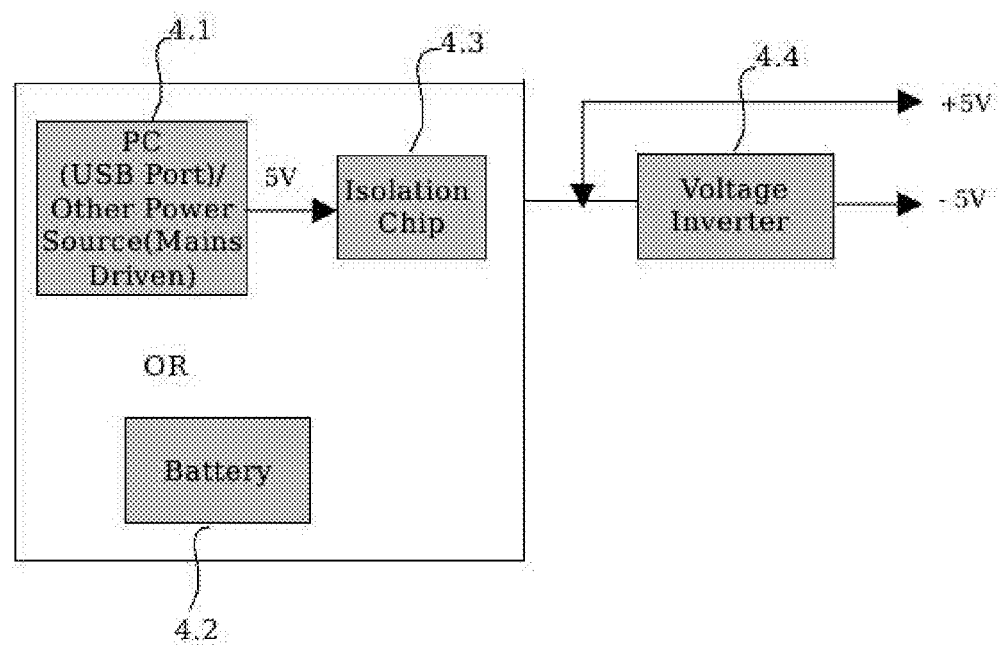
FIG. 5 is a block diagram illustrating the Power Unit.
Figure 6:
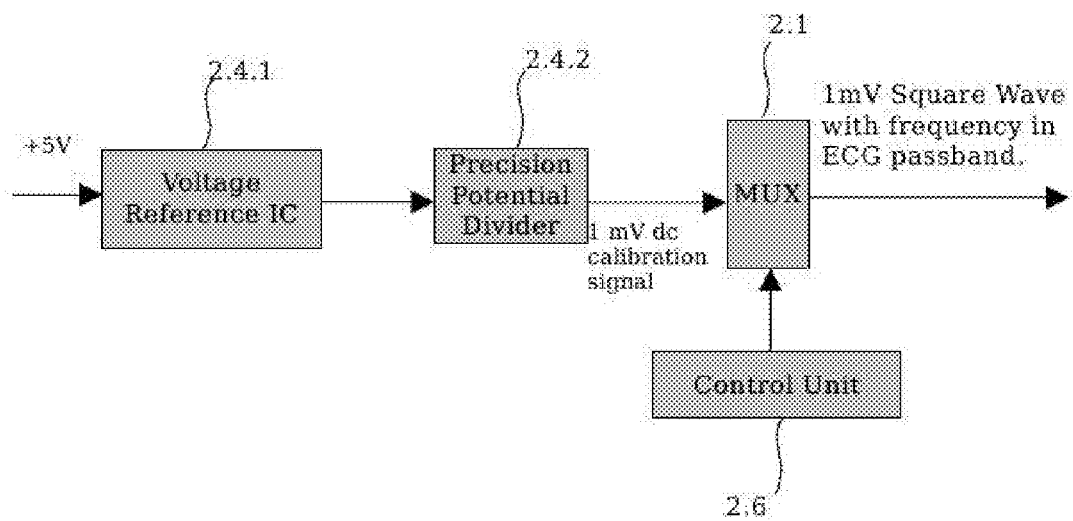
FIG. 6 is a block diagram illustrating the Calibration Unit.

Referring first to FIG. 2, it illustrates, by means of block diagram, the portable, high quality, reliable, low cost, efficient ECG monitoring device comprising of ECG electrodes and leadwires (1), ECG module (2), User Interface (3), and Power Unit (4). ECG leadwires (1) are connected to the patient by means of electrodes and an ECG is measured as the potential difference between a pair of electrodes attached to the body of the patient e.g. on his/her arms and legs and the chest. The measured signals are supplied to ECG module (2) for signal conditioning and amplification as well as for filtering the different noises present in the signal to get the desired signal. The interactive user interface module (3) is used as an interface with the user. The power unit (4), as shown in FIG. 5, consists of (4.1), a power source which can be the USB port of a PC/laptop, or any other external power source, or an external battery unit (4.2), with a voltage output of nominally 5V/3V. In case the power source involves connections to the ac mains, directly or indirectly, an isolation chip, (4.3), is used as a safety feature. A voltage inverting IC, (4.4), is used to generate a bipolar power supply. This power unit, (4) then supplies power to the whole ECG device.

By a preferred method of the invention, ECG monitoring device is deriving power from USB interface of personal computer or laptop.

Figure 3:
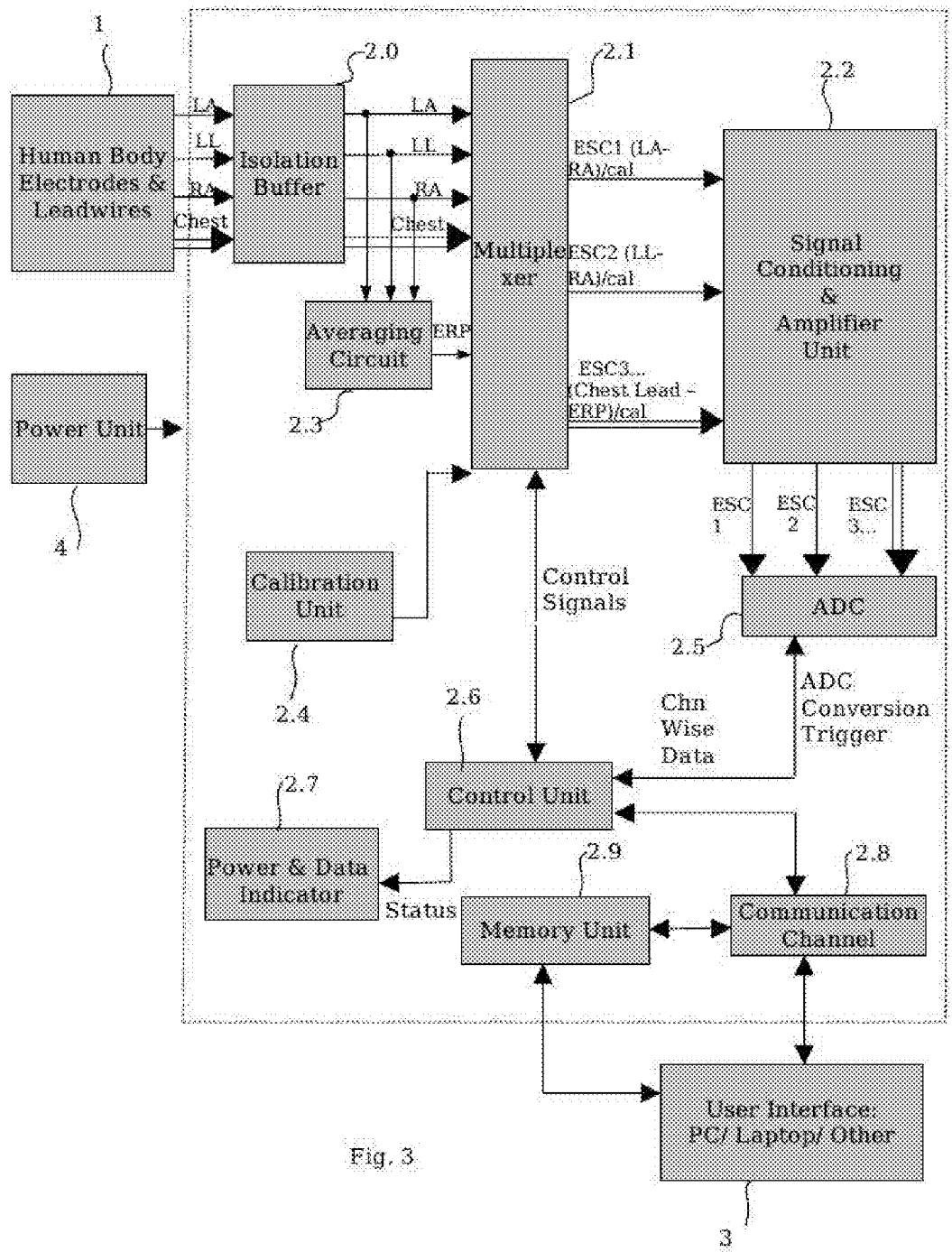
FIG. 3 is a block diagram illustrating the ECG Module of the monitoring device.
Figure 4:
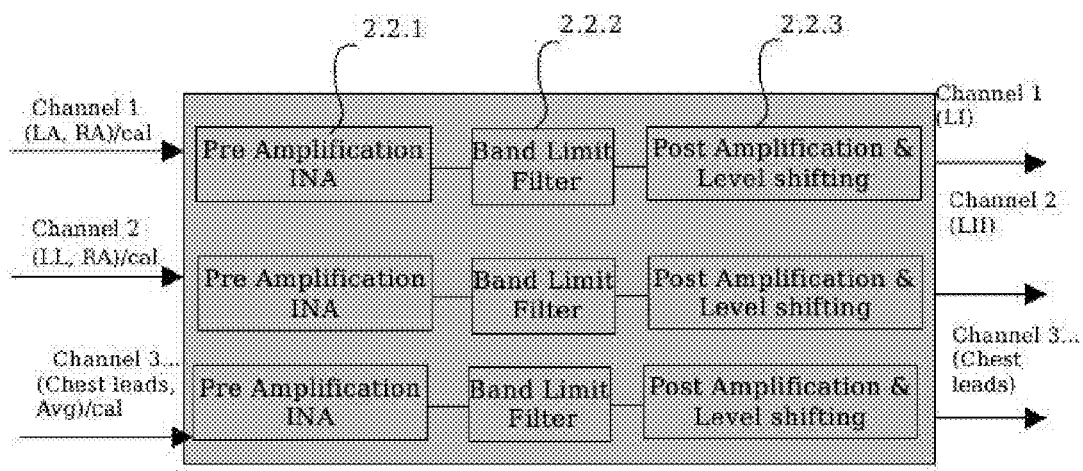
FIG. 4 is a block diagram illustrating the Signal Conditioning and Amplifier Unit.

Referring to FIG. 3, ECG Module (2) consists of Isolation Buffer (2.0), Multiplexer (2.1), Signal Conditioning and Amplifier Unit (2.2), Averaging Circuit (2.3), Calibration Unit (2.4), Analog to Digital Converter (2.5), Control Unit (2.6), Power and Data Indicator (2.7), Communication Channel (2.8) and Memory Unit (2.9).

As soon as the ECG Module (2) is powered by the power unit (4), the Control Unit (2.6) automatically initializes all the hardware components of the ECG device, including communication bus, timers, etc and configures an interrupt for ECG data sampling. A 1 mV dc output is generated as a calibration signal by Calibration Unit (2.4), chopped via the multiplexer unit (2.1) to convert the 1 mV DC into a 1 mV ac signal at a frequency falling within the ECG pass band (say 10 Hz), and fed to the circuit along the same route of amplifiers and filters etc., as that for an ECG signal. Control unit (2.6) now waits for the start command from the user. Upon receipt of the start command electrical signals picked up by the electrodes (1) are routed through the isolation buffer (2.0) and also through an averaging circuit (2.3). Calibration signal, and ERP and ECG signals from the electrodes are provided as input to the multiplexer (2.1) in order to arrange routing of signals of the three (three in this preferred embodiment) respective ESCs for input to the Signal Conditioning and Amplifier unit (2.2). The output, in the required frequency range typically from 0.22 Hz to 100 Hz and typical gain of 1000, from the Signal Conditioning and Amplifier unit (2.2), is then applied to the ADC of high enough precision 2.5. The output of the ADC is fed into control unit (2.6), for removal of impulsive and channel switching ADC noise by using a novel method of 'Burst Sampling' and correction for sequential non simultaneous sampling of the measured ECG leads. The Control Unit (2.6) sends the digitized ECG signals through the communication channel (2.8) to the user interface module (3). A detailed description of the various units shown in FIG. 2 is as follows:

Electrodes, Isolation Buffer and Averaging Circuit: The ECG signals are picked up from the human body at (1), the electrodes attached to the body. These signals are fed into the Multiplexer unit (2.1) via the isolation buffer (2.0). The buffered signals from the left arm, right arm and the left leg, LA, RA, and LL are also fed to an averaging circuit (2.3). The isolation buffer converts the ECG signals with high source impedance (of the human body) to ECG signals of low source impedance (of the output of the isolation buffer) to ensure no loss of signal at subsequent signal conditioning and preamplification stages which have a finite input impedance. The averaging circuit (2.3) averages the buffered voltages from LA, RA, and LL to provide the ERP with respect to which the chest lead signals can be measured.

Self Calibration Unit: The self calibration unit, 2.4, comprises a voltage reference IC, 2.4.1, powered by the power unit 4, used to generate a stable DC reference voltage (typically 2.5 V). This voltage is stepped down to 1 mV by using, a precision resistive voltage divider 2.4.2. This 1 mV DC output is used as a calibration signal. It is fed to-the MUX 2.1. During the calibration cycle, the Control Unit, (2.6), chops this 1 mV DC input at a frequency in the pass band of the ECG monitoring device (typically 10 Hz). The 1 mV, 10 Hz, square wave thus generated at the output of the MUX (2.1) is fed into each ESC of the signal conditioning and amplifier unit (2.2), and undergoes the same signal conditioning, amplification, ADC conversion and data acquisition by the controller as any normal ECG signal. The digital counts, for each ESC, corresponding to this 1 mV amplitude calibration signal are stored as calibration constants by the control unit, (2.6). Thus, no external calibration signal source is required to calibrate this ECG module and the device is self calibrating.

Signal Conditioning & Amplifier Unit: The first stage of the Signal Conditioning and Amplifier Unit (2.2), is an instrumentation amplifier (INA) (2.2.1). It has a high common mode rejection ratio (CMRR) for eliminating the common mode noise, such as the 50 or 60 Hz AC interference. The gain is typically set to 10. It is then followed by a combination of simple first order high pass and low pass analog filters to limit the frequency band of the ECG signal. This band limit filter (2.2.2) passes signals in the frequency range 0.22 Hz to 100 Hz. The high pass filter filters out DC offsets to prevent saturation of subsequent amplification stages and also attenuates low frequency drifts in the ECG signals. The cut off frequency (0.22 Hz) of the high pass filter is chosen to be equal to or less than the lower limit of the ECG pass band. The low pass filter attenuates high frequency noise and also serves as an anti aliasing filter for digitized ECG signals. The maximum value of the cut off frequency of the low pass filter is the sampling frequency of the ECG signals (200 Hz in the preferred embodiment) minus the upper frequency limit of the ECG pass band of frequencies. A post amplification stage with a typical gain value of 100 combined with a DC level shift is implemented at the Post Amplification and Level Shifting unit (2.2.3), in the second stage of amplification. The DC level shift, derived from the Voltage Reference (2.4.1), raises all amplified signals above 0 V. This is necessary only for compatibility with unipolar input ADCs. The human ECG signal is very small (in the 1 mV range). The total gain of the circuit is about 1000 so that the ECG is in the right voltage range for measurement by the analog to digital converter (ADC). The output of the various ESCs, which are the selected ECG signals after signal conditioning and amplification from the Signal Conditioning and Amplifier Unit (2.2), are input to different built-in input channels of the ADC unit (2.5). For battery operated units where the operating voltage is less the 5 volts (typically 3 volts), the post amplification gain can be limited to, say, 500 so as not to exceed the dynamic range of the amplifiers.

Analog to Digital Converter (ADC) Unit: The ECG signals from the Signal Conditioning and Amplifier Unit, (2.2), are input into various input channels of the ADC unit, (2.5). This unit consists of an IC and has preferably 12 bit or higher resolution and has a minimum number of input channels equal to the number of ESCs. The ADC input channel selection signals and ADC conversion trigger are received from the control unit, (2.6). The digitized data is also communicated to the control unit (2.6).

Control Unit: The control unit, (2.6), may include any one or a combination of a micro controller, microprocessor, digital signal processor (DSP), application specific integrated circuit (ASIC), field programmable gate array (FPGA), or other digital logic circuitry. This unit is responsible for controlling, monitoring, and reading data from other units in the device via a uni or bi-directional communication as applicable.

By a preferred method of this invention, this ECG module is using a micro controller. It performs the following major tasks:

sends control signals to the MUX (2.1), to connect to ground all ESCs when the ECG module is in the initialization stage;

sends control signals to the MUX (2.1), when the ECG module is self calibrating, converting the 1 mV dc signal from the calibration unit (2.4) to a 10 Hz square wave and output it on all ESCs connected to the Signal Conditioning and Amplifier Unit (2.2);

sends control signals to the MUX (2.1), when the ECG module is in the ECG acquisition state, to connect the ECG signals to the ESCs of the Signal Conditioning and Amplifier Unit (2.2);

sends control signals to, the ADC (2.5), to configure the ADC and trigger ADC conversions at the desired sampling rate;

Manages the SPI bus to read data from the ADC;

Keeps track of power supply status and error conditions if any;

Controls status indicators for power and device run state in unit (2.7);

Implements communications with the memory unit (2.9) and the user interface unit (3), as applicable. The communication can be over SPI, USB, USART, RS-232, BLUETOOTH, ZIGBEE, ethernet, etc.

Checks for underflow and overflow of ADC for clip detection.

Applies linear interpolation for correcting errors due to non simultaneous sequential sampling of ECG leads from which derived leads are calculated.

Stores acquired ECG data in a temporary data buffer.

Once the data buffer is full, a data frame is built by adding a header and footer to the data in case the data is to be communicated to an external device (e.g., PC/laptop). This is another aspect of the present invention whereby the digitized data of the measured ESC is framed into a data frame which helps in error detection/correction which may occur during communication to any external device.

The header, along with starting delimiter, has information on the data length and type, and error correction codes. The footer has end delimiter characters.

Memory Unit: The memory unit (2.9) may consist of a unit integrated into the ECG module, or a pluggable unit which can be taken out and read on an external PC/laptop, or be the data storage on a PC/laptop itself.

Power and Run State Indicator: This unit, (2.7), has simple LED indicators controlled by the Control-Unit (2.6) to visually indicate the error status of the power supply and the run state of the ECG module.

Communication Channel: The communication channel (2.8) can be any one or a combination of SPI, USB, USART, RS-232, bluetooth, zigbee, ethernet, etc. By a preferred method of this invention, USB interface is used to communicate with the PC/laptop. SPI interface is used to communicate with ECG module inbuilt memory, LCD display and keypad, if any.

User Interface: The user interface (3) includes a visual graphics display and an input device like a keypad/keyboard/mouse. These can be inbuilt into the ECG module or be an external PC/laptop/mobile phone, etc.

Figure 7:
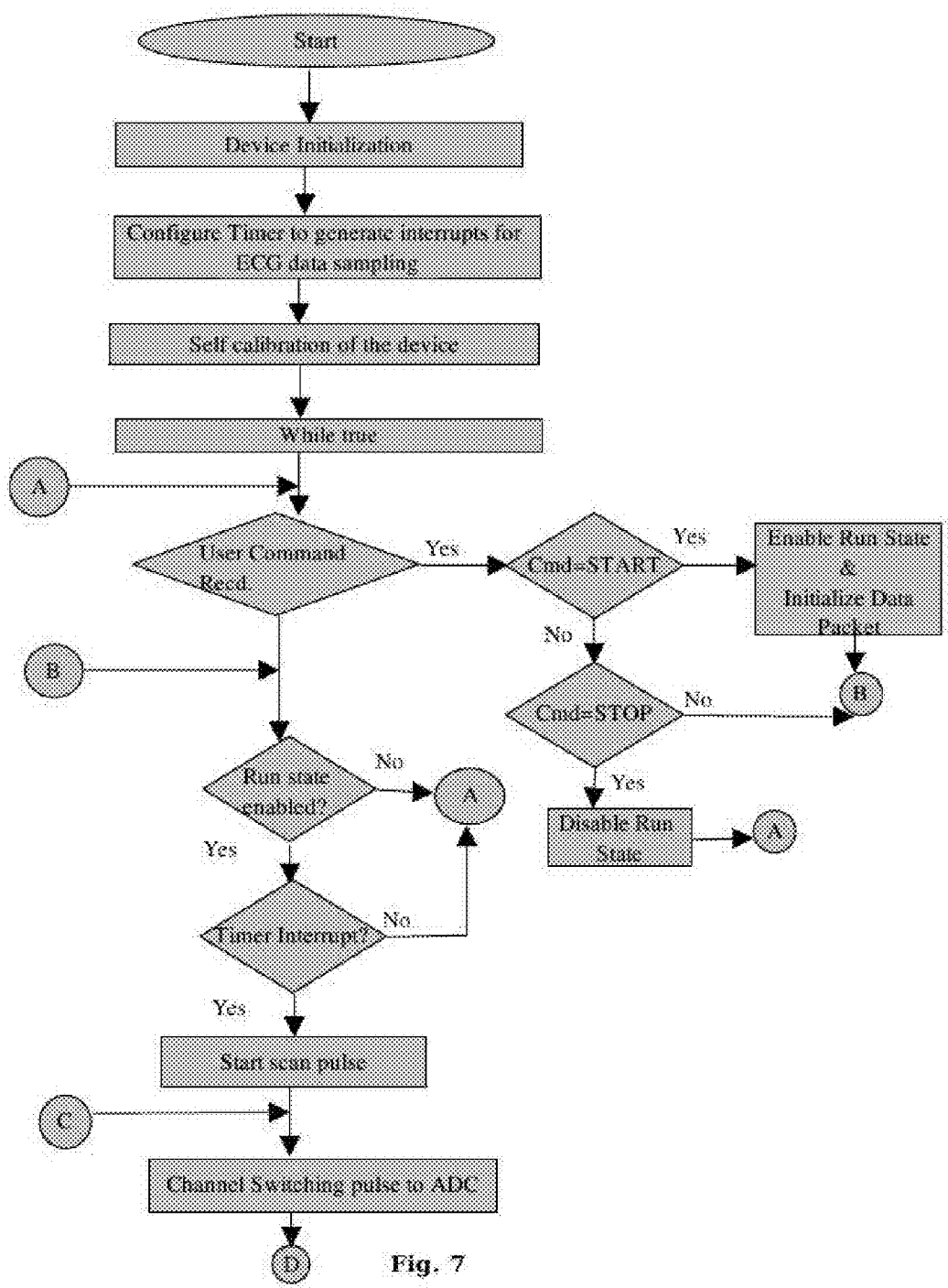
FIG. 7 is the flow diagram showing the principle of operations carried out by the micro controller in the ECG monitoring device.
Figure 7:
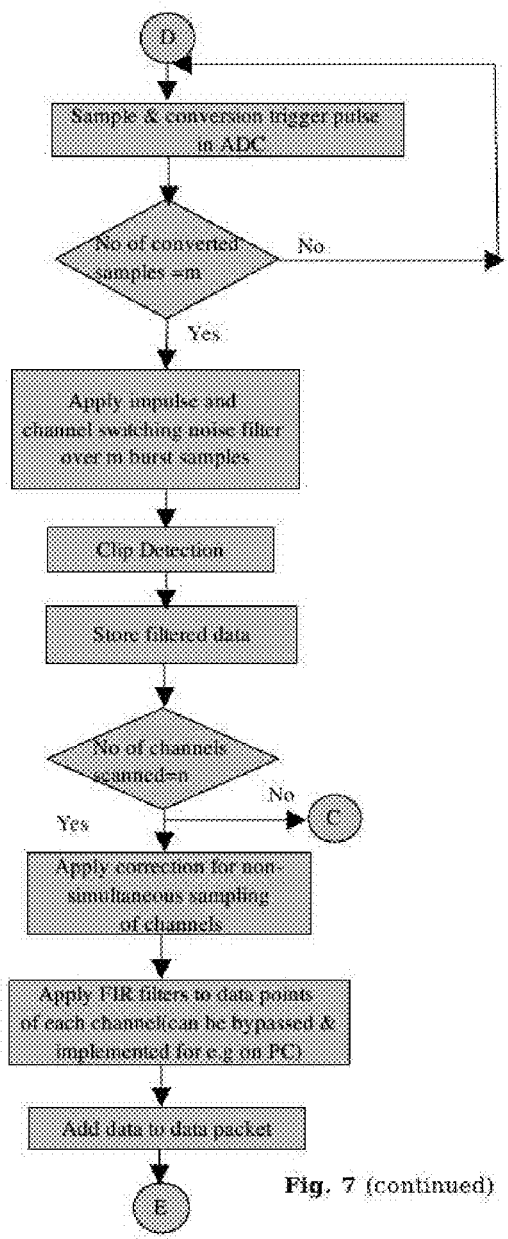
Figure 7:
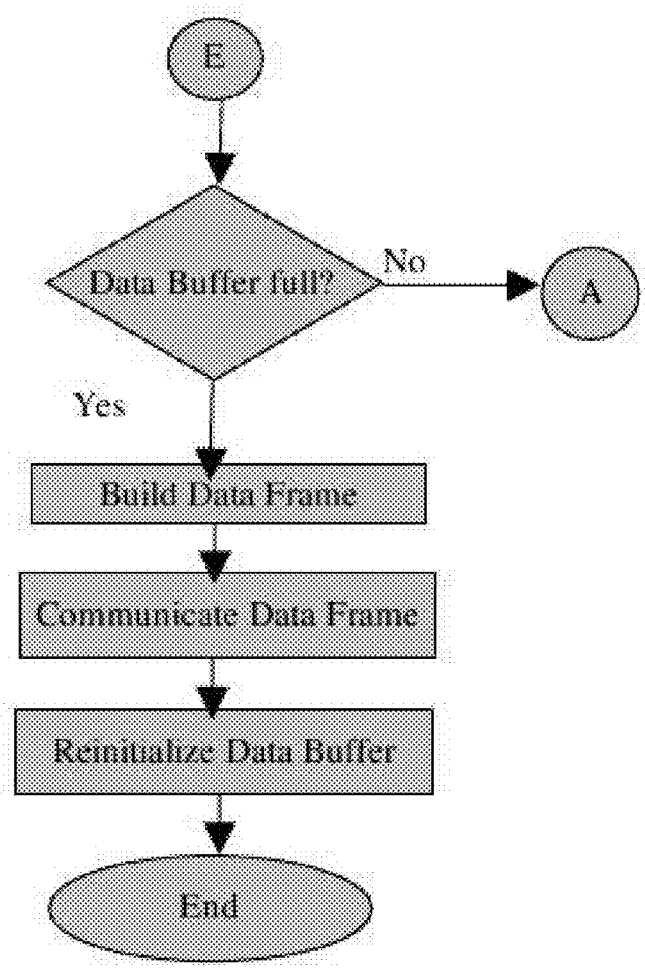

Firmware: FIG. 7 is a flow chart showing the principle of operations carried out by the firmware in the ECG monitoring device.

Figure 9:
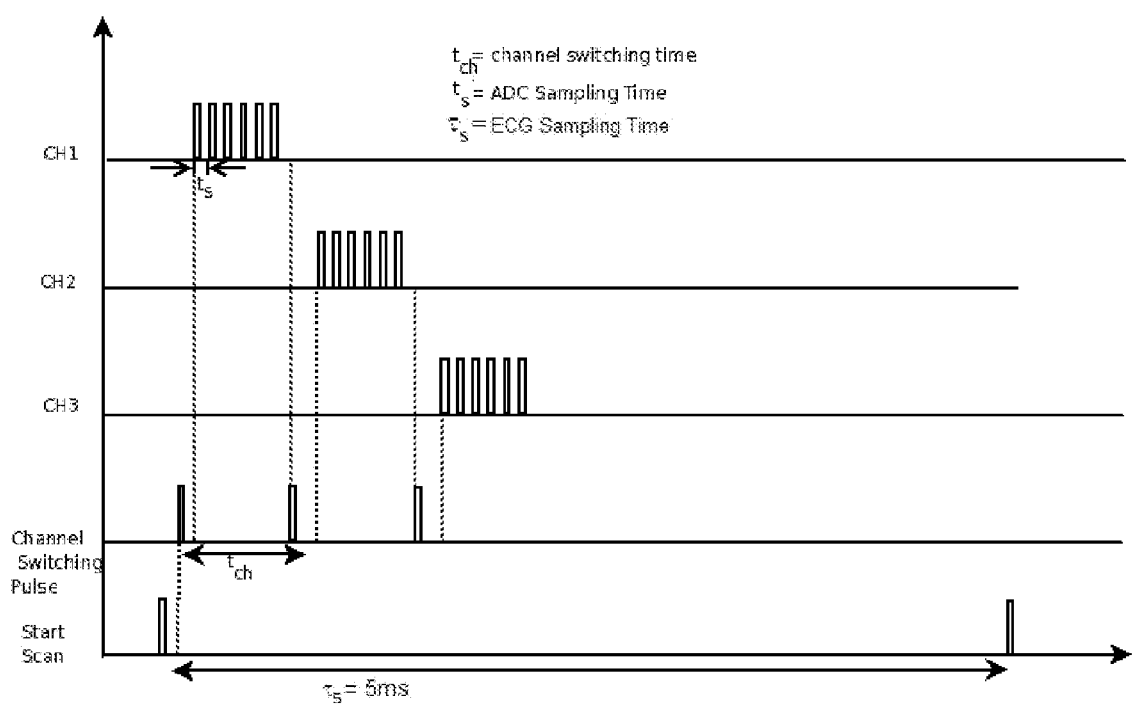
FIG. 9 is the timing diagram the principle of operation of the Burst Sampling.
Figure 10:
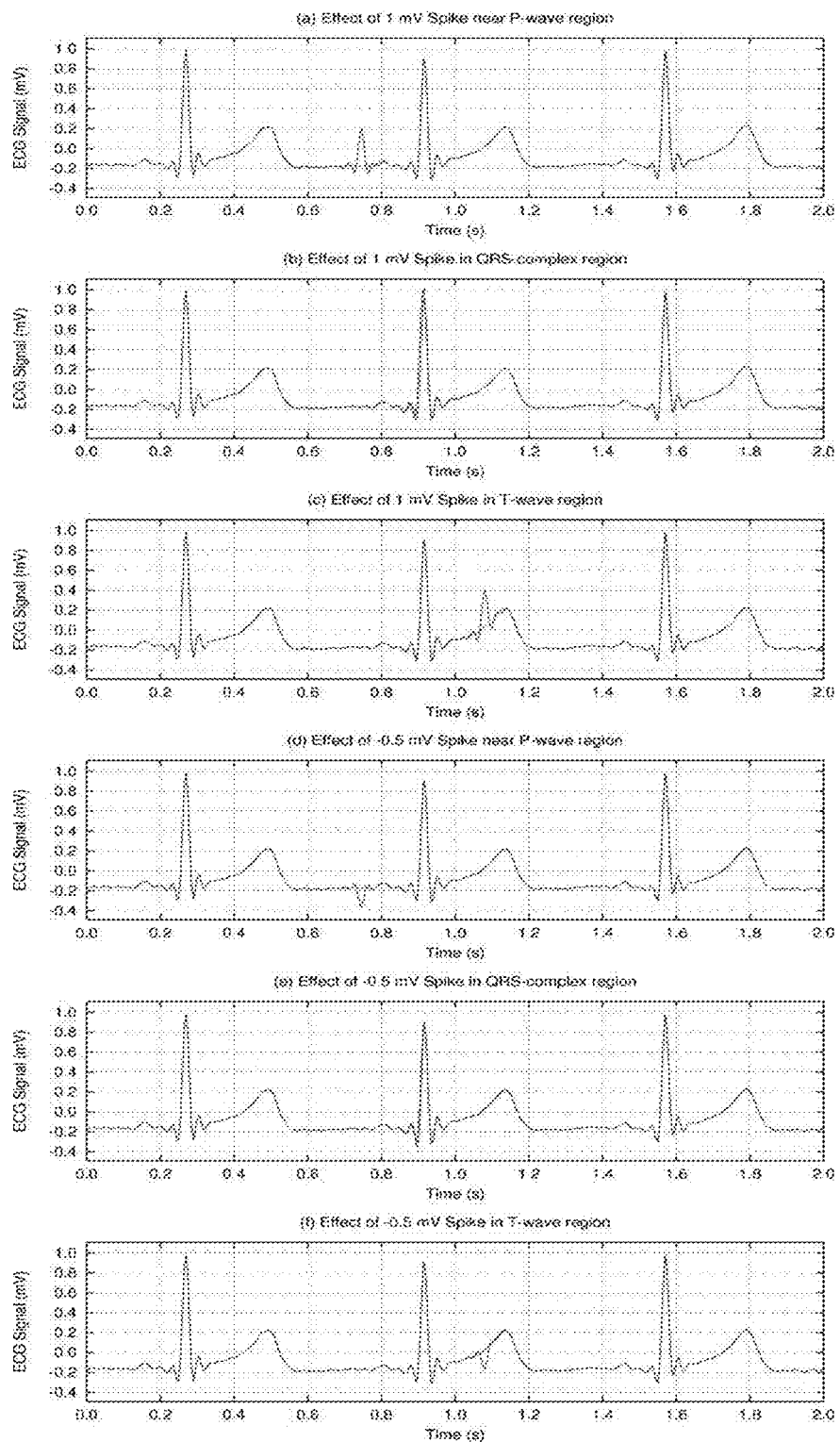
FIG. 10 is an example illustrating the effect of impulse noise on different segments of an ECG signal.

Upon switching ON the device, the initialization of communication buses, ADC, timers, etc., is carried out. The timer is pre-configured to generate a periodic interrupt with a time period $\tau_s$ (5 ms in the preferred embodiment) equal to the ECG data sampling frequency. Each interrupts triggers a scanning cycle whereby signals from all ESCs are measured by the ADC in a sequential manner. The device is then self calibrated using the 1 mV 10 Hz square wave signal as explained in the Calibration Unit section. The device then waits for a command from the user. Upon the receipt of a START command from the user, the RUN State is enabled, the Data Buffer is initialized and the interrupt timer, used for scanning cycles, started. Following operations, as shown in the timing diagram in FIG. 9, are further performed when a START command is received from the user.

A start scan pulse is generated by a timer interrupt in the control unit to start a scanning cycle. These timer interrupts are generated with the sampling frequency of the ECG data (ECG sampling time $\tau_s$=5 ms in this case).

The control unit then sends the channel selection pulses to the ADC at an interval of $t_{ch}$, the channel switching time. The number of such pulses is equal to n, the number of ESCs to be measured (n=3 in this case). The ESC selection pulses sequentially scan all the ESCs to be measured by the ADC. Upon receipt of an ESC selection pulse, the ADC switches its measurement circuitry to a particular ESC and samples that particular ESC in a burst of m sampling pulses (m=8 in this case). The sampling time of the ADC, i.e., the time between two consecutive sampling pulses in a burst is denoted by $t_s$. The following relationships exist amongst the various time periods in the scheme outlined above, $$mt_s \leq t_{ch}$$

$$nt_{ch} \ll \tau_s \quad (3)$$

where n is the total number of ESCs being measured. The first inequality provides for enough time for m samples to be measured in a burst by the ADC within the ESC scan time available, $t_{ch}$. The second inequality provides for enough time, between the end of an ESC scan and the beginning of the next scanning cycle, for processing of data digitized by the ADC. These relationships between the various time intervals are also depicted in the timing diagram at FIG. 9.

Impulse and channel switching ADC noise filter, which uses "Burst Sampling", is then applied over m digitized samples for each of the n ESCs to remove noise consisting of high frequency spikes/glitches in the ECG voltage signal according to the following algorithm.

Burst Sampling Algorithm:—Let $y_j^i$ be the $j^{th}$ digitized reading for ESC i measured with time interval $t_s$. The m measured values for this ESC i are sorted and the median $y_{median}^i$ and the mean $<y^i>$ of the m values is computed. A weighted average of the median and mean is calculated to give one filtered digitized value, $\bar{y}^i$ for the ESC. The weight factors for the mean, w, and the median, (1−w), sum up to unity.

$$\bar{y}^i = w<y^i> + (1-w)y_{median}^i \qquad (4)$$

The rationale behind this procedure is that as the m readings for a given ESC i are taken in quick succession at time intervals of $t_s$, it is assumed that the underlying ideally measured distribution in the short interval of time $t_{ch}$ is symmetric. A trimmed mean is a robust estimator because it is less sensitive to outliers which are still taken into account with less weight age. In case the distribution is asymmetric, then the median gives a measure of the average "completely" insulated from outliers. Hence, we take a weighted average of both the mean and the median to accommodate both possibilities.

In a practical implementation of the above algorithm, in case the sorting of the m digitized values is time consuming, we discard the maximum and minimum digitized values and take the mean of the remaining m−2 values. This gets rid of one each of the minimum and maximum outlier as the median operation does and the subsequent mean operation averages the remaining measurements.

As the derived leads are computed by taking appropriate linear combinations of the measured signals, it is important that the measured signals correspond to the same instant of time. However, in the digitization scheme presented in FIG. 9, it can be seen that the set of readings in each scanning cycle for the n ESCs are not measured simultaneously, but with a time delay of $t_{ch}$ between two consecutive ESCs. An error corrector is applied utilizing an interpolation scheme to compute values of the signals from the n ESCs interpolated to the same instant of time. The derived leads are then computed from these interpolated signal values thus avoiding errors in the derived leads due to non simultaneous sequential sampling of different ESCs.

The Correction algorithm for non simultaneous sampling of ESCs—The filtered digitized value $\bar{y}^i$ for ESC i corresponds to a time ($it_{ch}$) relative to the time at which the first ESC is measured in a given scanning cycle. First of all, to minimize such corrections, all the filtered digitized values $\bar{y}^i$ for the n ESCs in a given scanning cycle are interpolated to a reference time, ($i_0 t_{ch}$) corresponding to the measurement of ESC number $i_0 = n/2$. The corrected and filtered interpolated value $y_c^{-i}(i_0 t_{ch})$ is given, in terms of the current filtered value $\bar{y}^i(i_0 t_{ch})$ and the filtered value in the previous scanning cycle $\bar{y}^i(i_0 t_{ch} - t_s)$, by the linear interpolation formula:

$$\bar{y}_c^i(i_0 t_{ch}) = \bar{y}^i(it_{ch}) + (i - i_0)[\bar{y}^i(it_{ch}) - \bar{y}^i(it_{ch} - \tau_s)]\frac{t_{ch}}{\tau_s} \qquad (5)$$

While, a linear interpolation formula is described here, in case the corrections are large due to large values of $t_{ch}/t_s$ or large changes in signal from one scanning cycle to the next, or both, higher order interpolation can be used. However, this would require measured values of $\bar{y}^i$ for even earlier scanning cycles.

The digital filters as explained in the 'Digital filter' section are then applied to the sampled data points to remove various types of noise like base line wandering, power line interference and its harmonics, EMG noise etc. Optionally, these digital filters can be applied after the data is communicated to an external device like a PC/laptop.

The processed and filtered data is then added to the data frame which is then transmitted over the communication channel to external device.

The data is displayed on the User Interface device and may be recorded for future reference and analysis.

Digital Filter Unit: In one aspect of the present invention, a real time digital FIR filter implemented in firmware is used to remove baseline wandering, power line interference and its harmonics, EMG noise etc to ensure that only ECG data are recorded with the exclusion of noise. Digital filtering brings about many benefits. For example, digital filters implemented in firmware/software save space and weight which the conventional analog filters require. Digital filters are easily programmed and easily adjusted and readjusted. Digital filters are generally more reliable than their analog counterparts. Digital filters may also be inexpensive. The digital filtering can alternatively be implemented externally (for example, on a PC, laptop, etc.). In this case the data frames with unfiltered data are communicated to the external computing device which can then implement the filters and other user interface, etc.

The overall filtering mechanism is as follows. Firstly, the band limit filter implemented in the signal conditioning stage of the device filters out dc offsets and frequencies above the Nyquist frequency (100 Hz in this case), which is a few times higher than the upper frequency of the ECG pass band. This is a first order analog filter. Due to the non-linear nature of analog filters, only an order one filter is used to prevent distortion of the ECG signal. The attenuation in the stop band is consequently limited (to that of a first order filter). This filter would also filter out high frequency spikes/glitches/impulses picked up by the analog electronics before the amplification stage. However, it would not filter such spikes/glitches/impulses introduced after the amplification stage, e.g., at the ADC stage.

Secondly, the filtering effected by the invented burst sampling scheme filters out spikes/glitches/impulses of duration equal to or less than the burst sampling time, $t_s$, completely, as one outliers each of maximum and minimum amplitudes are discarded from the m samples in a burst. It spikes/glitches/impulses of longer duration (a few times the burst sampling period, but smaller than the total burst period) by averaging over the measured samples in the total burst period (typically 0.5-1.0 ms, depending upon the number of ESCs measured in the available ECG sampling time).

Thirdly, the linear FIR filters provide an effective ECG bandpass filter to remove the low frequency noise like baseline wander and higher frequency noise like EMG noise (typically in the frequency range 32-40 Hz), power-line noise (50/60 Hz) and other noise in the stop band. As the Nyquist frequency is typically 100 Hz (for an ECG sampling time of 5 ms) and the upper pass band frequency is 32 Hz (in this case) the frequencies beyond 100 Hz, not removed effectively by the first stage and first order analog filter and aliased into the desired stop band (0-0.3 Hz and 32-100 Hz) are also removed very effectively. The attenuation, if not complete removal, of the spikes/glitches/impulses by the burst sampling scheme, helps reduce the ringing effects of the FIR filter.

Storage and Recording: In one aspect of the invented system, a measured ECG can be immediately processed upon recording. In addition to measuring and recording an ECG, another aspect of the present invention includes obtaining an earlier measured and stored electrocardiogram from a storage location for processing and display.

Figure 8:
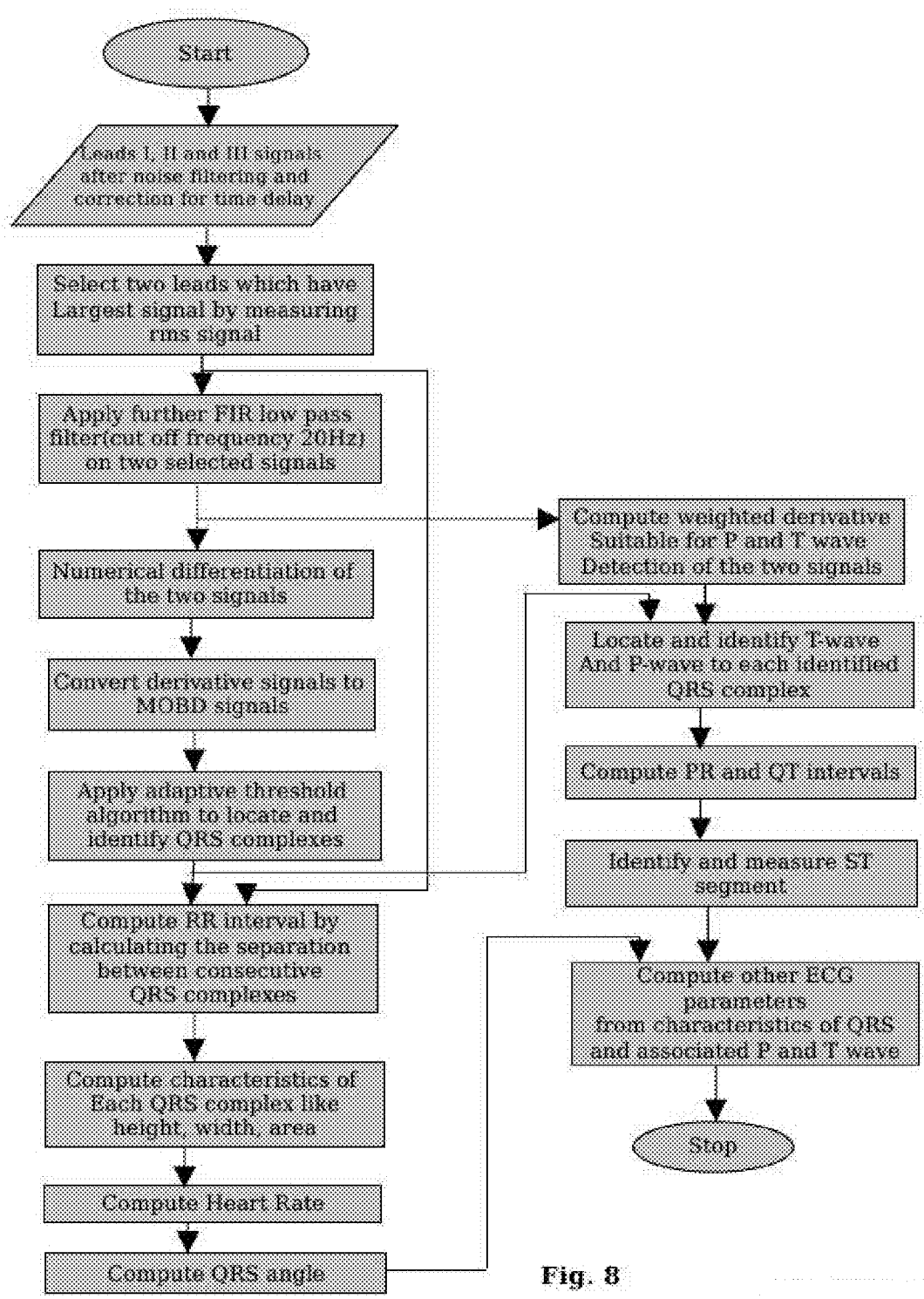
FIG. 8 is the flow diagram showing the steps done in analysis and parameter extraction software.

Extraction of ECG Parameters: The steps involved in extracting various ECG parameters are shown in a flow diagram in FIG. 8. The algorithm and method used for extraction of parameters is largely based on the work "Parameter Extraction of ECG Signals in Real Time" by U. Kunzmann, G. von Wagner, J. Schöchlin, A. Bolz, Biomed Tech (Berl). 2002; 47 Suppl 1 Pt 2, pp. 875-878. The inputs to the parameter extraction scheme are the Lead I, II, and III digitized signals from the ECG device after noise filtering and correction for time delays due to sequential sampling. The following steps are applied to these digitized signals:

(a) Choose two the Lead I, II, and II signals with the largest r.m.s. Value.
(b) Apply a further low pass digital FIR filter with a cut off frequency of 20 Hz for further smoothening of signals.
(c) Numerically differentiate these two signals.
(d) Convert the derivative of signals from step (c) to multiplication of backward differences (MOBD) signal for reliable detection of QRS complexes and eliminating false short duration peaks in the derivative signal.
(e) Use an adaptive thresholding scheme and locate and identify QRS complexes whose MOBD signal exceeds the thresholds.
(f) Once the QRS complexes are located, characterize them by measuring their width, height, area, etc from the original signals before the application of the low pass filter in step (b).
(g) Compute from the location and characteristics of the QRS complexes, the RR interval and hence the heart rate and the QRS angle.
(h) For detection of P and T waves associated with each QRS complex, compute weighted derivatives with weights favoring shapes of P and T waves. Once the P and T waves are located and the ST region identified, compute parameters such as the intervals PR, QT, QTc and ST elevation.
(i) Compute average and standard deviation of all measured parameters.

FIG. 10(a)-(f) show the results of the efficiency of our filtering method based on burst sampling to filter impulsive ADC noise in an ECG signal. The Lead I ECG signal of a subject as measured by the ECG device is taken and an impulse of 1 mV or –0.5 mV is introduced near the P-wave region, or QRS complex region, or the T-wave region. The two cases of the size of impulse are chosen with respect to the typical amplitude of 1 mV for a QRS complex. FIGS. 10 (a)-(c) are for a 1 mV impulse noise introduced while FIGS. 10 (d)-(f) are for an impulse noise of –0.5 mV. The sets (a), (b), (c) and (d), (e), (f) correspond to introduction of impulse noise in the P-wave, QRS-complex, and the T-wave region, at time instants 0.55 s, 0.92 s, and 1.4 s, respectively. The blue traces show the ECG signal with an introduced impulse noise filtered using FIR filters alone without the application of the invented burst sampling method. The red traces show the same traces after the impulse noise are filtered using the invented burst sampling method. These red traces coincide with the original measured traces without the introduction of any impulse noise, thus confirming the effectiveness of the filtering based on the burst sampling technique. Near the region of the introduction of the impulse noise the blue traces show that the ECG signal develops oscillations distorting the measured ECG signal very significantly. The impulse noise shows up as a local oscillatory feature in the trace because of the bandpass FIR filter allowing only the frequency components of the impulse in the pass band of the FIR filter. As the results show, the filtering method used in this invention for filtering impulse noise is very effective.

Figure 11:
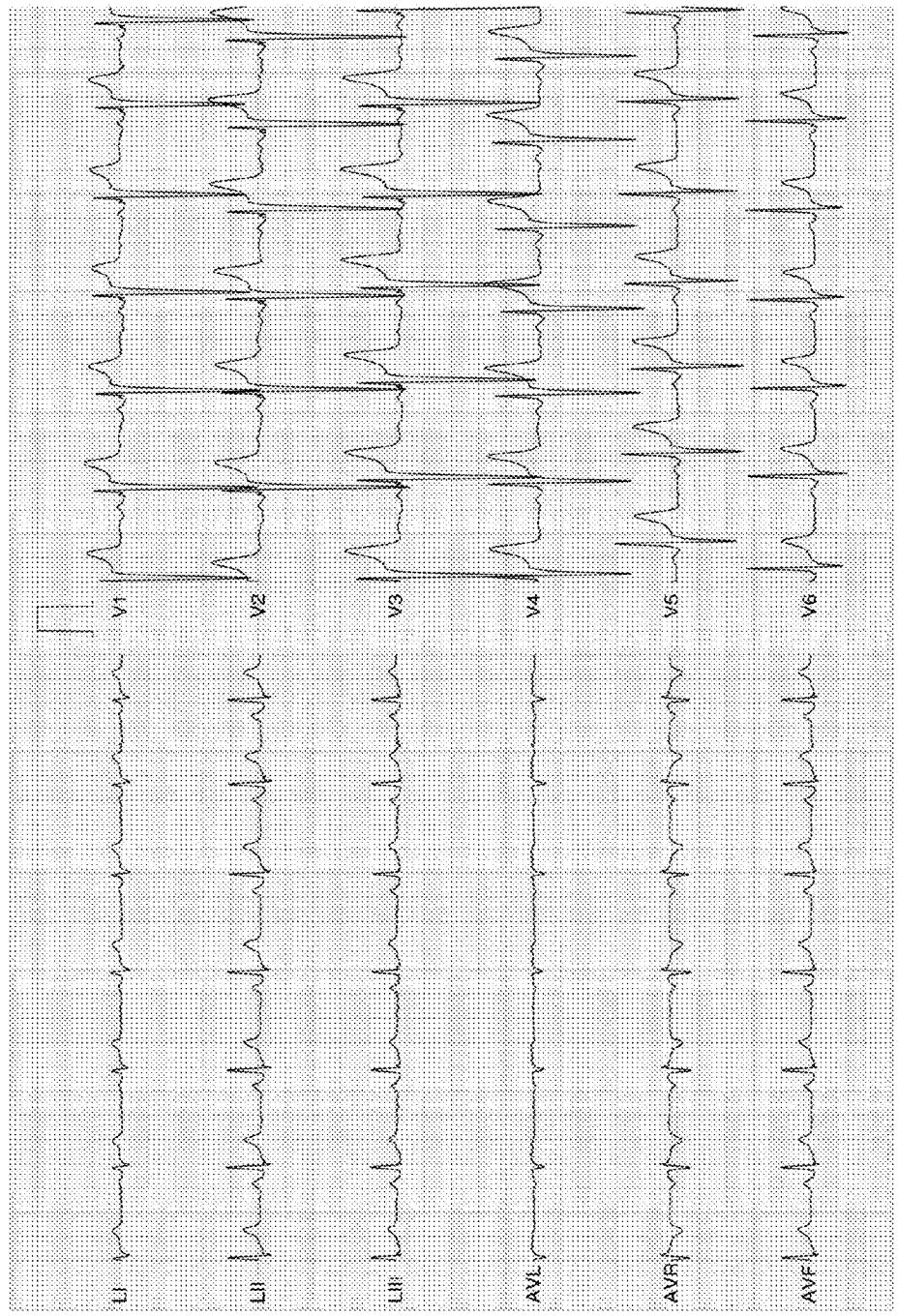
FIG. 11 is a printed ECG recording of a patient showing the parameters extracted and displayed thereof.

FIG. 11 shows the high quality of a full 12-lead printed record of an ECG as measured by the 5-electrode version of the device invented. In this device, Leads I, II and V1 are measured simultaneously, Leads III, aVL, aVR and aVF are derived from Leads I and II. Leads V2-V6 are measured by physically moving the chest lead to the appropriate location on the chest. The values of some of the extracted ECG parameters, along with their standard deviations, are also shown.

Figure 12:
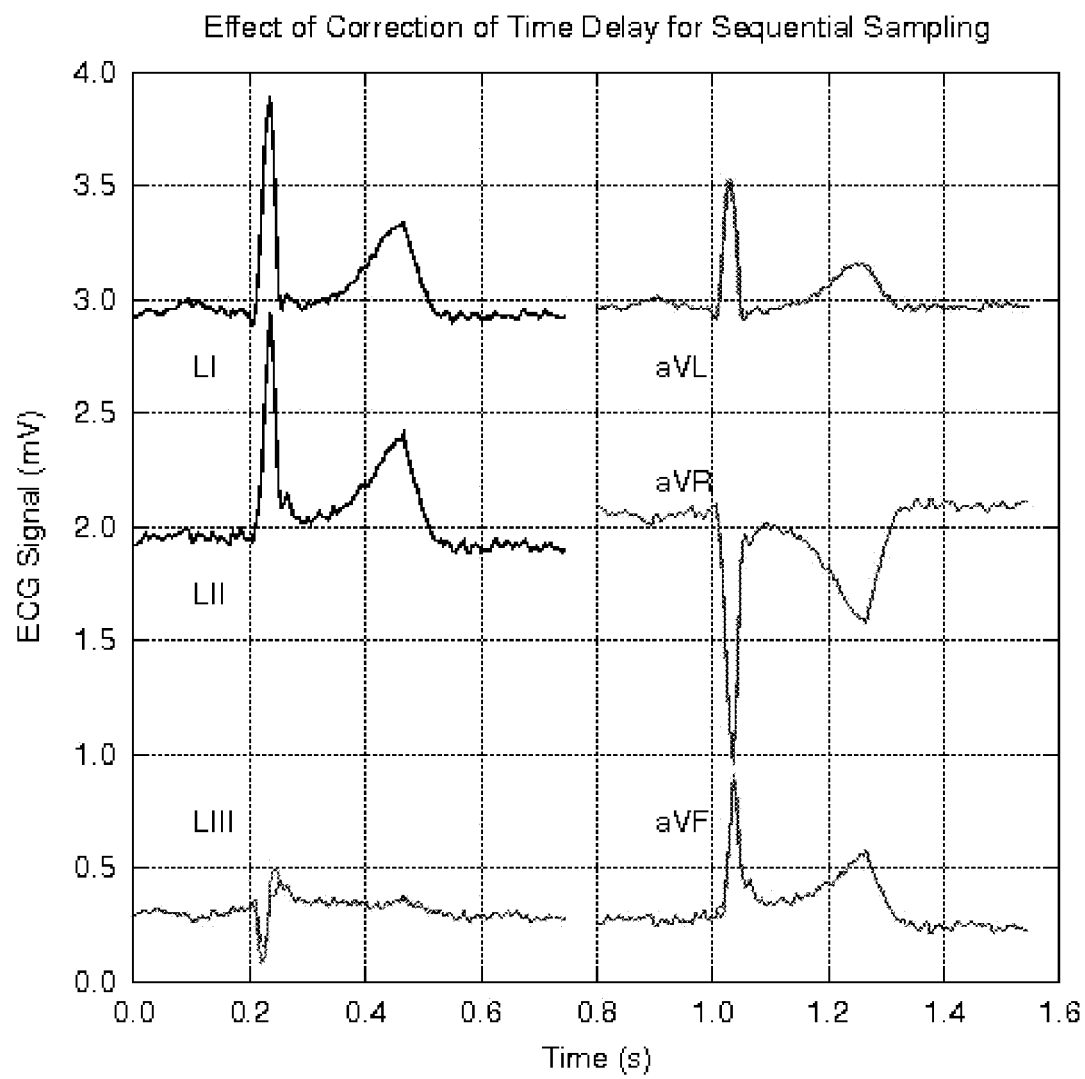
FIG. 12 is an ECG recording showing the results of application of corrections for time delays to the derived leads' signals.
Figure 13:
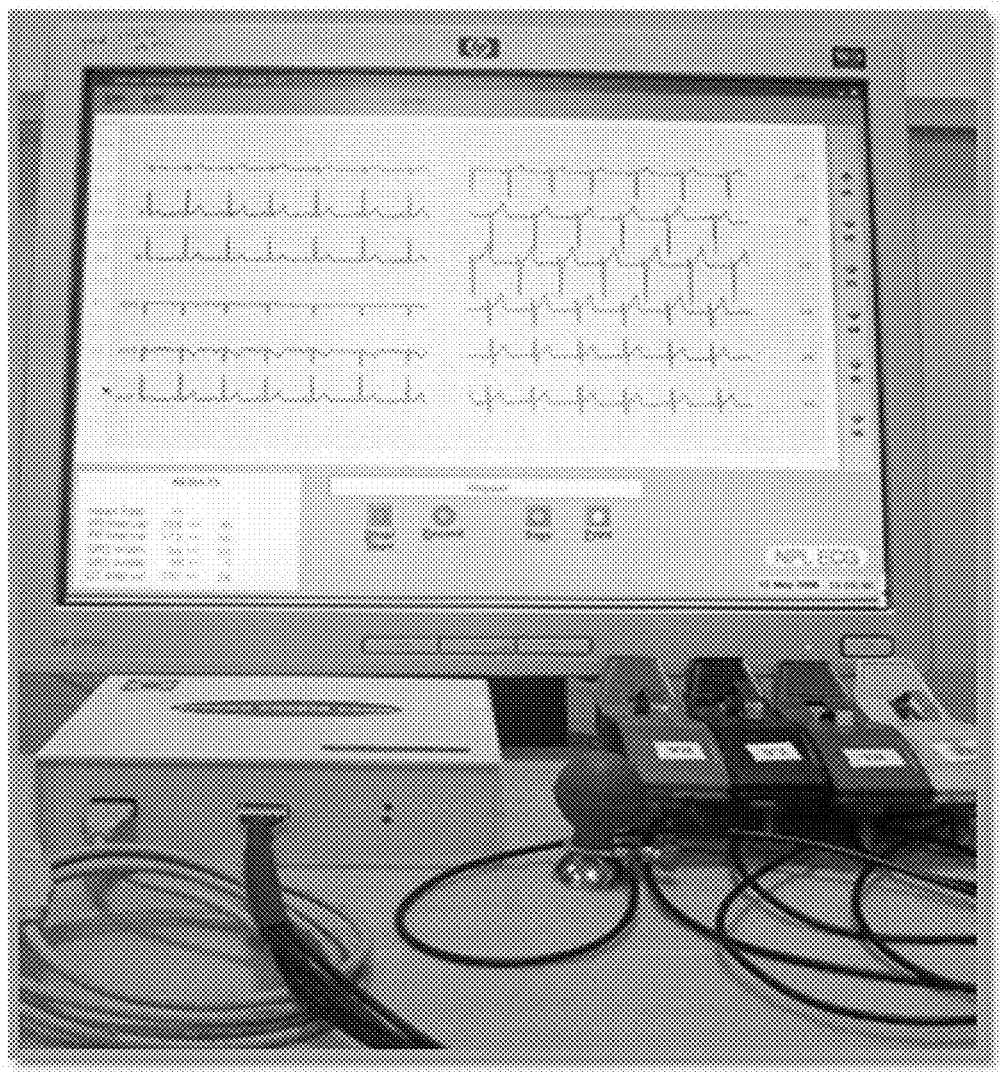
FIG. 13 is the photograph of the ECG Monitoring Device.

FIG. 12 shows the results for the derived leads, LIII, aVR, aVL, and aVF, from direct measurements on leads LI and LII. Leads LI and LII which are measured directly by the ECG device sequentially are shown in black traces. The derived lead signals LIII, aVL, aVR, and aVF are shown, with (red traces) and without (blue traces), the utilization of the scheme invented to correct for the time delays due to sequential sampling of different ECG signals. The results shown are for a typical burst sampling frequency of 5 kHz and 8 (super) samples (m=8) per ESC (ECG signal) in a burst. As can be seen from the results, the errors can be significant for the QRS-complex. For lead LIII, the correction in the QRS complex amplitude is of the order of 50% for the set of timing parameters mentioned above. The errors are large where the slope of the ECG signal is large. Hence, for QRS-complexes of shorter duration, the errors would be even larger.

The invention provides an ECG device with a rich set of features including self calibration, efficient noise filtering and ECG parameter extraction facility.

The invention provides an ECG device that is compact, light weight and highly cost effective due to reduced number of hardware components.

The invention provides an ECG device with improved maintainability as up gradation of firmware is simpler than re-building the circuitry/hardware.

The invention provides an ECG device with improved accuracy of Derived ECG Leads.

The invention provides an ECG device with multi operating system support for end user software.

The invention provides an ECG device with facility to store and retrieve ECG data as well as patient information.

We claim:

1. An electrocardiograph (ECG) device, comprising:
a) a plurality of ECG electrodes adapted to receive respective cardiac signals from the body of a subject;
b) a plurality of electronic signal channels (ESCs) electrically connected to selected ones of the plurality of electrodes and adapted to provide ECG voltage signals corresponding to the cardiac signals;
c) an analog-to-digital converter (ADC) operatively connected to the plurality of ESCs and adapted to:
  i) receive a selection of one of the ESCs;
  ii) capture a plurality of time-separated samples of the ECG voltage signal from the selected ESC; and
  iii) provide a plurality of digital values corresponding to the captured plurality of time-separated samples from the selected ESC;
d) a firmware storing an algorithm for a burst sampling technique;

e) a control unit responsive to the algorithm and adapted to:
   i) provide successive selections of the ESCs to the ADC, so that respective pluralities of digital values are provided for each ESC;
   ii) process the respective pluralities of digital values to provide a respective interpolated digital value for each ESC, wherein the respective interpolated digital value for each of the ESCs is interpolated to a common selected reference time; and
   iii) process each of the respective interpolated pluralities of digital values through a high order FIR filter using convolution techniques, so that noise is reduced;
f) a power unit for providing electrical power to the control unit; and
g) a user interface module coupled to the control unit.

2. The ECG device according to claim 1, further including:
a calibration unit adapted to provide a calibration signal in a selected pass band of the ECG device; and
an isolation buffer and a multiplexer electrically connecting the ECG electrodes to the respective ESCs, wherein the isolation buffer provides respective buffered cardiac signals corresponding to the cardiac signals and the multiplexer selectively provides to each of the ESCs either a signal derived from the respective buffered cardiac signal or the calibration signal;
wherein the control unit is further adapted to:
cause the multiplexer to provide the calibration signal to each of the ESCs;
ii) provide successive selections of the ESCs to the ADC, so that respective pluralities of calibration digital values are provided for each ESC; and
iii) store the respective pluralities of calibration digital values.

3. The ECG device according to claim 2, wherein the calibration unit provides a 1 mV AC signal at a frequency falling within the selected pass band.

4. The ECG device according to claim 2, wherein the multiplexer selectively provides to the ESCs either the respective buffered cardiac signal or the calibration signal.

5. The ECG device according to claim 1, wherein the cardiac signals include a left-arm (LA) cardiac signal, a right-arm (RA) cardiac signal, and a left-leg (LL) cardiac signal, the ECG device further including:
an isolation buffer electrically connecting the ECG electrodes to the respective ESCs, wherein the isolation buffer provides respective buffered cardiac signals corresponding to the cardiac signals; and
an averaging circuit electrically connected to the isolation buffer to receive buffered LA, RA, and LL signals corresponding to the LA, RA, and LL cardiac signals, respectively, and adapted to produce an average of the buffered LA, RA, and LL signals as an Einthoven's Reference Potential (ERP) signal.

6. The ECG device according to claim 5, wherein the cardiac signals further include a chest signal, the plurality of ESCs includes three ESCs, and the ECG device is arranged so that the LA signal minus the RA signal is provided to a first one of the ESCs, the LL signal minus the RA signal to a second one of the ESCs, and the chest signal minus the ERP signal is provided to a third one of the ESCs.

7. The ECG device according to claim 1, wherein each of the plurality of ESCs includes a respective instrumentation amplifier, a respective band-limit filter, and a respective post-amplification and level-shifting unit electrically connected in series in that order.

8. The ECG device according to claim 1, wherein the control unit is further adapted to select each of the respective pluralities of digital values in turn, and, for each selected plurality of digital values:
compute a mean and a median of the selected plurality of digital values; and
produce a weighted average of the computed mean and the computed median as a respective filtered digitized value for the ESC corresponding to the selected plurality of digital values.

9. The ECG device according to claim 8, wherein the control unit is adapted to produce the weighted average by forming a linear combination of the mean and the median with respective weight factors that sum to unity.

10. The ECG device according to claim 8, wherein the control unit is further adapted to remove a minimum digitized value and a maximum digitized value from each selected plurality of digital values before computing the mean of the selected plurality of digital values.

11. The ECG device according to claim 8, wherein the control unit is adapted to:
repeatedly provide selections, compute means and medians, and produce weighted averages for a plurality of scanning cycles, so that a plurality of filtered digitized values are provided, one filtered digitized value for each of the ESCs in each of the scanning cycles; and
process the respective pluralities of digital values to provide the respective interpolated pluralities of digital values by:
   i) selecting two consecutive ones of the scanning cycles;
   ii) for each of the ESCs, determining a respective trend using the filtered digitized values corresponding to the selected scanning cycles and to that one of the ESCs; and
   iii) for each of the ESCs, interpolating the respective trend to the selected reference time to provide the respective interpolated digital value for that ESC.

12. The ECG device according to claim 11, wherein the selected reference time is a midpoint of the latter of the selected scanning cycles.

13. The ECG device according to claim 1, the user interface module having a visual display, wherein the control unit provides the respective interpolated digital values to the user interface module, which displays them on the visual display.

14. The ECG device according to claim 1, further including a user input device, wherein the control unit is responsive to a start command received via the user input device to provide the successive selections.

15. The ECG device according to claim 1, further including a memory unit adapted to store the respective interpolated digital values.

16. The ECG device according to claim 1, further including a communication channel, wherein the control unit is further adapted to transmit the respective interpolated digital values via the communication channel.

* * * * *